(12) United States Patent
Holland et al.

(10) Patent No.: US 7,229,605 B2
(45) Date of Patent: Jun. 12, 2007

(54) NUCLEI DENSITY AND NUCLEI AREA METHODS FOR DETERMINING EFFECTS OF A BOTULINUM TOXIN ON MUSCLES

(75) Inventors: James M. Holland, Dana Point, CA (US); Edward Chow, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 34 days.

(21) Appl. No.: 10/918,845

(22) Filed: Aug. 13, 2004

(65) Prior Publication Data

US 2005/0019338 A1 Jan. 27, 2005

Related U.S. Application Data

(63) Continuation-in-part of application No. 10/208,165, filed on Jul. 29, 2002, now Pat. No. 6,984,375.

(60) Provisional application No. 60/309,988, filed on Aug. 3, 2001.

(51) Int. Cl.
*A61K 49/00* (2006.01)

(52) U.S. Cl. .................. 424/9.2; 424/184.1; 424/247.1

(58) Field of Classification Search .................. None
See application file for complete search history.

(56) References Cited

U.S. PATENT DOCUMENTS

| | | | |
|---|---|---|---|
| 5,158,976 A | 10/1992 | Rosenberg | |
| 5,183,462 A | 2/1993 | Borodic | |
| 5,298,019 A | 3/1994 | Borodic | |
| 5,401,243 A | 3/1995 | Borodic | |
| 5,548,661 A | 8/1996 | Price et al. | |
| 5,696,077 A | 12/1997 | Johnson et al. | |
| 5,766,605 A | 6/1998 | Sanders et al. | |
| 5,856,665 A | 1/1999 | Price et al. | |
| 6,143,306 A | 11/2000 | Donovan | |
| 6,235,289 B1 | 5/2001 | Aoki et al. | |
| 6,306,403 B1 | 10/2001 | Donovan | |
| 6,358,926 B2 | 3/2002 | Donovan | |
| 6,365,164 B1 * | 4/2002 | Schmidt .................. 424/239.1 |
| 6,416,765 B1 | 7/2002 | Donovan | |
| 6,416,959 B1 | 7/2002 | Giuliano et al. | |
| 6,429,189 B1 | 8/2002 | Borodic | |
| 2003/0032069 A1 | 2/2003 | Muraca | |

FOREIGN PATENT DOCUMENTS

WO  9903483  *  1/1999

OTHER PUBLICATIONS

Adler, M et al, Toxicon, vol. 39, pp. 233-243, 2001.*

(Continued)

*Primary Examiner*—Mark Navarro
*Assistant Examiner*—Ginny Allen Portner
(74) *Attorney, Agent, or Firm*—Claude L. Nassif; Stephen Donovan; Martin A. Voet

(57) ABSTRACT

Methods for determining the effect of a Clostridial neurotoxin on muscle are disclosed. In particular, methods for determining a potency and/or diffusion of a neurotoxin based on a nuclear index and/or an amount of muscle atrophy are disclosed. The methods may be used to distinguish two different Clostridial neurotoxins. In certain embodiments, the neurotoxins are obtained from *Clostridium botulinum*.

12 Claims, 17 Drawing Sheets

OTHER PUBLICATIONS

Aoki, K. Roger, European J. of Neurology, vol. 6(suppl. 4), pp. S3-S10, 1999.*
Borodic, Gary E. et al, Ophthalmic Plastic and Reconstructive Surgery, vol. 9(3), pp. 182-190.*
Dodd, SL et al, Eur. J. Neurol., Mar. 1998, vol. 5(2) pp. 181-186.*
Duchen, LW, J. of Neurological Sciences, pp. 47-74, 1971, vol. 14(1).*
Inagi, K et al, The Laryngoscope, vol. 108 (7), Jul. 1998, pp. 1055-1061.*
Tang, Xiaofu et al, Chinese Medical Journal, 2000, vol. 113(9), pp. 794-798.*
Sampaio, C et al, Movement Disorders, vol. 12(6), pp. 1013-1018, 1997.*
Aoki, K.R., *Preclinical update on Botox® (botulinum toxin type A)—purified neurotoxin complex relative to other botulinum neurotoxin preparations*, European Journal of Neurology 1999, 6 (suppl 4):S3-S10.
Barry, B.W., *Novel mechanisms and devices to enable successful transdermal drug delivery*, European Journal of Pharmaceutical Sciences, 14 (2001) 101-114.
Bigalke, H., et al., *Botulinum A neurotoxin inhibits non-cholinergic synaptic transmission in mouse spinal court neurons in culture*, Brain Res. 1985;360:318-24.
Bigalke, H. et al., *Tetanus toxin and botulinum A toxin inhibit release and uptake of carious transmitters, as studied with particulate preparations from rat brain and spinal cord*, Naunyn Schmiedebergs Arch Pharmocol, 1981:316-244-51.
Boyd, R.S., et al., *The insulin secreting -cell line. HIT-15 contains SNAP-25 which is a target for botulinum neurotoxin-A*, Movement Disorders, vol. 10, No. 3, 1995, pp. 376.
Garcia, A., et al., *Cosmetic denervation of the muscles of facial expression with botulinum toxin*, Dermatol Surg 1996, 22: pp. 39-43.
Gonelle-Gispert, C., et al., *SNAP-25a and 25b isoforms are both expressed in insulin-secreting cells and can function in insulin secretion*, Biochem. J. (1999) 339, 159-165.
Habermann, E., et al., Tetanus toxin and botulinum A anc C neurotoxins inhibit noradrenaline release from cultured mouse brain, J. of Neurochemistry, 51, 522-527 (1988).
Habermann, E., *Inhibition byb tetanus and botulinum A toxin of the release of [$^3$H ]noradrenaline and [$^3$H ] GABA from rat brain homogenate*, Experientia 1988 Mar 15:44(3):224-6.
Jankovic, J. et al., *Therapy with Botulinum Toxin*, Marcel Dekker, Inc., 1994, p. 5.
Li, F., et al., *Formation of binucleated cardiac myocytes in rat heart II. Cytoskeletal organization*, J. Mol Cell Cardiolo 29, 1553-1565 (1997).
Lim, D.A., et al., *Interaction between astrocytes and adult subventricular zone precursors stimulates neurogenesis*, Proc. Natl. Acad. Sci. USA, vol. 96, pp. 7256-7531, Jun. 1999, Neurobiology.
Luna, L.E., *Manual of histologic staining methods of the armed forces institute of pathology.* $3_{rd}$ ed., 1968 Chapter 6, McGraw-Hill, pp. 72-99.
Manual of Histologic and Special Staining Technics, McGraw-Hill Book Co., The Blakiston Division 2 $^{nd}$ Ed., (1960) Chp. 6, *Stains for Connective Tissue*, pp. 55-95.
Marchese-Ragona, R., et al., *Management of Parotid Sialocele with Botulinum Toxin*, The Laryngoscope, Aug. 1999, 109, pp. 1344-1346.
Marjarma-Lyons, et al., *Tremor-predominant Parkinson's disease*, Drugs and Aging Apr. 2000 16(4):273-278.
Naumann, M., et al., *Botulinum toxin type A in the treatment of focal, axillary and palmar hyperhidrosis and other hyperhidrotic conditions*, European Journal of Neurology, 1999 6 (suppl 4): S111-S115.
Pearce, L.B., et al., *Pharmacologic characterization of botulinum toxin for basic science and medicine*, Toxicon, 1997 vol. 35, No. 9, pp. 1373-1412.
Pearce, L.B., et al., *Measurement of botulinum toxin activity: evaluation of the lethality assay*, Toxicology and Applied Pharmacology 128, 69-77 (1994).

Sesardic, D., et al., *Refinement and validation of an alternative bioassay for potency testing of therapeutic botulimun type A toxin*, Pharmacol Toxicol 1996; 78(5): 283-8.
Sanchez-Prieto, J., et al., *Botulinum toxin A blocks A blocks glutamate exocytosis from guinea-pig cerebral cortical synaptosomes*, Eur J. Biochem Jun. 1987 165(3):675-681.
Schantz, E., et al. *Standardized assay for chlostridium botulinum toxins*, J. Assoc of Anal Chem. 1978;61(1)pp. 96-9.
Schantz, E., et al., *Properties and use of botulinum toxin and other microbial neurotoxins in medicine*, Microbiological Reviews, Mar. 1992 p. 80-99, vol. 56, No. 1.
Singh, B.R., *Critical aspects of bacterial protein toxins*, Natural Toxins II, 1996 Plenum Press, NY, Chp. 4, pp. 63-84.
Voytik, S.L., et al., *Differential expression of muscle regulatory factor genes in normal and denervated adult rat hind limb muscles*, Developmental Dynamics (1993) 198:214-224.
Adler, M., et al., *Persistence of botulinum neurotoxin A demonstrated by sequential administration of serotypes A and E in rat EDL muscle*, Toxicon 39 (2001) 233-243.
Hamjian, J.A., et al., Abstract: *Serial neurophysiological studies of intramuscular botulinum A toxin in humans*, Database Medline PubMed ID: 7969239, Dec. 1994 (1994012).
Hogwei, D., et al., *Morphologic changes in extraocular muscles after injection botilinum A toxin*, Chin Ophthal Res. Apr. 2000, vol. 18, No. 2, pp. 140-142.
Pinter, M.J., *Axotomy-like changes in cat motoneuron electrical properties elicited by botulinum toxin depend on the complete elimination of neuromuscular transmission*, Journal of Neuroscience, Mar. 1991, 11(3): pp. 657-666.
Samuel, D.P., *Hemihypertrophy and a poorly differentiated embryonal rhabdomyosarcoma of the pelvis*, Medical and Pediatric Oncology 32:38-43 (1999).
Braun, T., et al., *Differential expression of myogenic determination genes in muscle cells: possible autoactivation by the Myf gene products*, EMBO Journal, vol. 8, #12 pp. 3617-3625, 1989.
Chomcczynski, P., et al., *Single-step method of RNA isolation by acid guanidinium thioyanate-phenol-chloroform extraction*, Analytical Biochemistry 162, 156-159 (1987).
David, R.L., et al., *Expression of a single transfected cDNA converts fibroblasts to myoblasts*, Cell, vol. 51, 978-1000, Dec. 24, 1987.
Koppe, R.I., et al., *cDNA clone and expression analysis of rodent fast and slow skeletal muscle troponin I mRNAs**, The Journal of Biological Chemistry, vol. 264, No. 24, Aug. 25, 1989 pp. 14327-14333.
Lehrach, H., et al., *RNA molecular weight determinations by gel electrophoresis under denaturing conditions, a critical reexamination*, Biochemistry, vol. 16, No. 21, 1977, pp. 4743-4751.
Wright, W.E., et al., *Myogenin, a factor regulating myogenesis, has a domain homologous to MyoD*, Cell, vol. 56, Feb. 24, 1989, pp. 607-617.
Ansved, T. Neurology, (United States) May 1997, vol. 48(5), pp. 1440-1442, Muscle fiber atropy in leg muscles after botulinum toxin type A treatment of cervical dystonia.
Bhatia, KP et al, J. Neurol. Neurosurg. Psychiatry, 1999, vol. 67, pp. 90-93.
Borodic et al., 1992, Botulinum and Tetanus Neurotoxins (ed BR DasGupta, Plenum Press, New York) pp. 623-645.
Chen, Chen-Ming et al., J. Appl. Physiol. vol. 93, pp. 1437-1447, Jun. 30, 2002.
Coffield, J.A. et al., The Journal of Pharmacology and Experimental Therapeutics, vol. 289, No. 3, pp. 1509-1516, 1999.
Doggweiler, R., et al., The Postate, vol. 37, pp. 44-50, 1998.
Ellies, M. et al., European Federation of Oto-Rhino-Laryngological Societies, 1999, vol. 256(3), pp. 148-152.
Ellies, M. et al., J. Oral Maxillofac. Surg. vol. 58, pp. 1251-1256, 2000.
Giovanoli, P., et al., Plastic and Reconstructive Surgery, Aug. 2000, vol. 106(2), pp. 383-392.
Hill, R.R., et al., Journal of Neurocytology, Mar. 1991, vol. 20(3), pp. 165-182.
Hott,. J.S., et al., Neurology, Feb. 1998, vol. 50(2), pp. 485-491.
Kranjc, B.S., et al., Investigative Ophthalmology & Visual Science, Dec. 2001, vol. 42(13), pp. 3158-3164.

Lu, L., et al., Plastic and Reconstructive Surgery, Jun. 1998, vol. 101(7), pp. 1875-1880.

Mendler, L., et al., Neromuscular Disorders, Dec. 1998, vol. 8(8), pp. 533-541.

Mohan, M., et al., Br. J. Ophthalmol., 1999, vol. 83, p. 1306+.

Ohishi, I., et al., Histopathological effect of botulinum C2 toxin on mouse intestines. Infection Immunity, vol. 43(1), pp. 54-58, 1984.

Palsson, E.M., et al., The Journal of Biological Chemistry, vol. 275(11), Mar. 17, pp. 7818-7825, 2000.

Parratte, B. et al., Surgical and radiological anatomy, (Germany), May 2002, vol. 24(2), pp. 91-96.

Rokx, J.T. et al., Acta anatomica (Switzerland), 1987, vol. 129(4), pp. 333-336.

Schwab, M.E., et al., (1976) Brain Research, Mar. 26, vol. 105(2), pp. 213-227.

Spencer, R.F., et al., Arch. Ophthalmol., vol. 105, Dec. 1987, pp. 1703-1711.

Trachtenberg, J.T., Developmental Biology, vol. 196, pp. 193-203, 1998, Fiber Apoptosis in Developing Rat Muscles is regulated by activity, neurogulin.

Van den Bergh, P., et al., Brain Reseach, vol. 707, pp. 206-212, 1996, Effect of muscle denervation on the expression of substance P in the ventral raphe-spinal pathway of the rat.

Witzemann, V., et al., FEBS Letters, (Netherlands) May 6, 1991, vol. 282(2), pp. 259-264, Differential regulation of MyoD and myogenin mRNA levels by nerve induced muscle activity.

* cited by examiner

Fig. 3. AVERAGE NUMBER NUCLEI VS. AVERAGE MUSCLE WEIGHT

Fig. 5A.   2101L OUTER
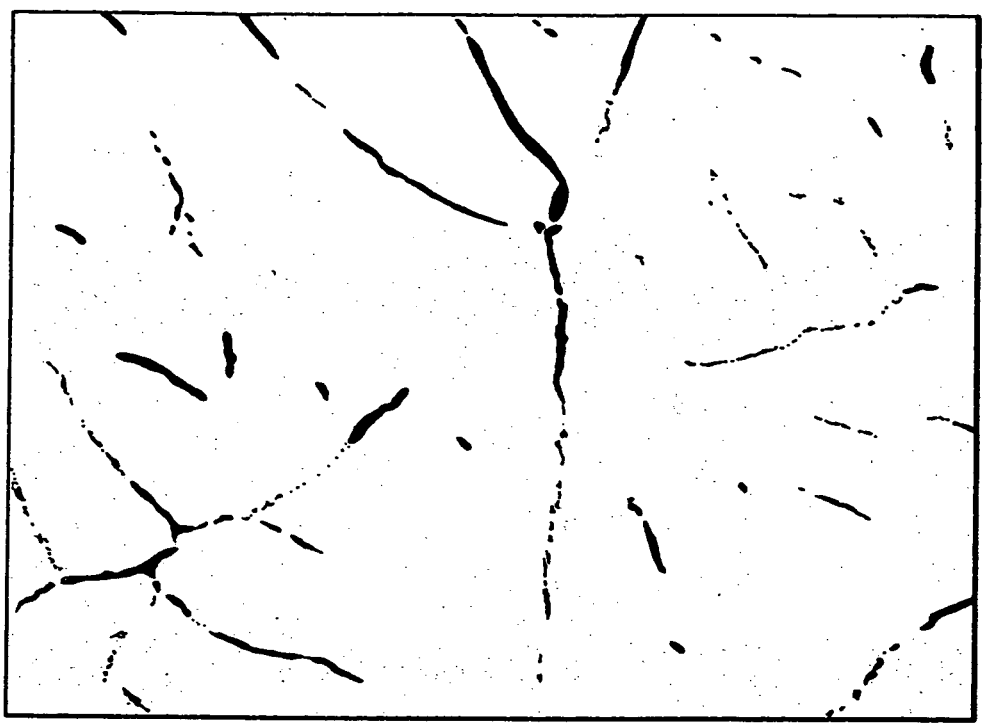
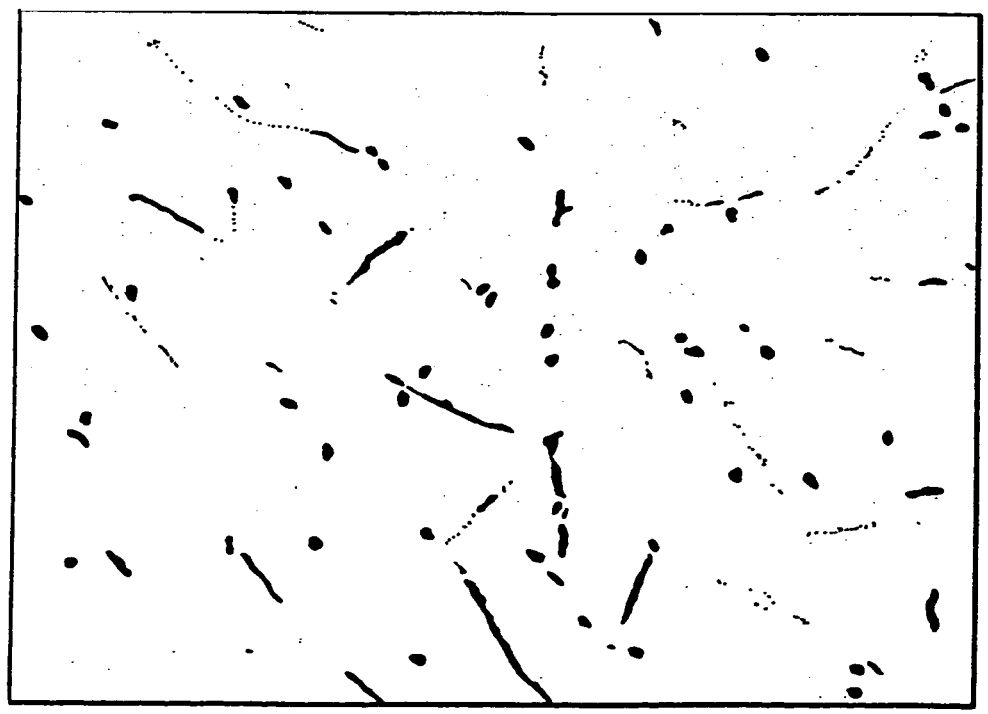
Fig. 5B.   2101L OUTER

FIG. 5C.

| STATS | AREA | DIAMETER (MEAN) | PER-AREA |
|---|---|---|---|
| MIN | 4.3060365 | 2.4406509 | .00002278 |
| (OBJ.#) | 25 | 25 | 25 |
| MAX | 45.520958 | 8.1463652 | .00024088 |
| (OBJ#) | 5 | 5 | 5 |
| RANGE | 41.214920 | 5.7057142 | .00021809 |
| MEAN | 11.391845 | 3.9377844 | .00006028 |
| STD. DEV | 5.8512273 | .99111760 | .00003096 |
| SUM | 1207.5355 | 417.40515 | .00638997 |
| SAMPLES | 106 | 106 | 106 |

CLASSIFICATION

FILE VIEW

| CLASS | OBJECTS | % OBJECTS | MEAN AREA | MEAN DIA. (MEAN) |
|---|---|---|---|---|
| 1 | 54 | 50.943394 | 7.5298672 | 3.2515821 |
| 2 | 36 | 33.962265 | 12.678884 | 4.2547326 |
| 3 | 11 | 10.377358 | 17.895216 | 5.1142292 |
| 4 | 3 | 2.8301888 | 24.195824 | 6.1818633 |
| 5 | 1 | .94339621 | 29.527107 | 5.7007999 |
| 6 | 0 | 0 | 0 | 0 |
| 7 | 0 | 0 | 0 | 0 |
| 8 | 1 | .94339621 | 45.520958 | 8.1463652 |
| 9 | 0 | 0 | 0 | 0 |
| 10 | 0 | 0 | 0 | 0 |

FIG. 5D.

FIG. 6A.   1400L OUTER
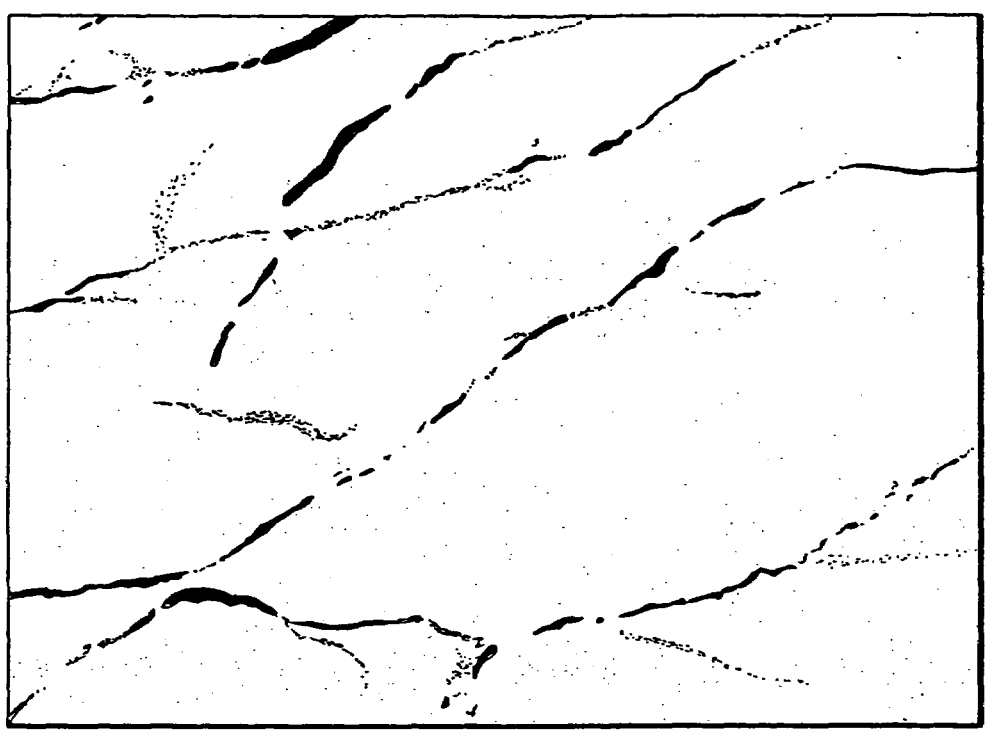
FIG. 6B.   1400 OUTER
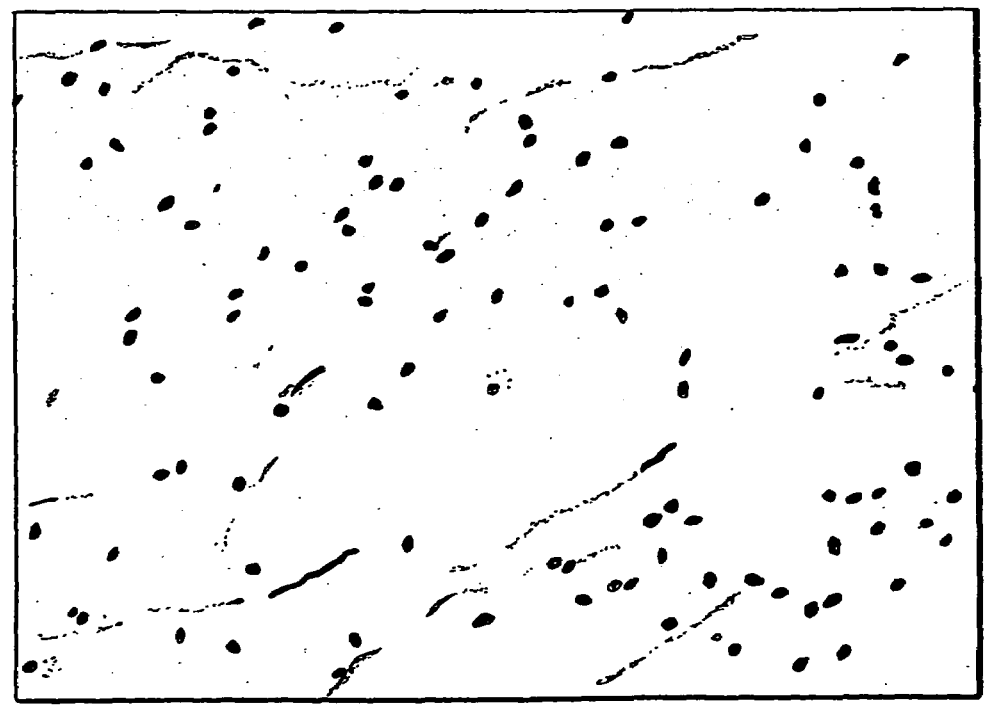

Fig. 6C.

| STATS | AREA | DIAMETER (MEAN) | PER-AREA |
|---|---|---|---|
| MIN | 4.3060365 | 2.3132176 | .00002278 |
| (OBJ.#) | 7 | 7 | 7 |
| MAX | 65.820847 | 11.660216 | .00034830 |
| (OBJ.#) | 229 | 114 | 229 |
| RANGE | 61.514809 | 9.3469982 | .00032552 |
| MEAN | 19.463675 | 4.9798832 | .00010299 |
| STD. DEV | 10.985473 | 1.4576392 | .00005813 |
| SUM | 3737.0254 | 956.13757 | .01977539 |
| SAMPLES | 192 | 192 | 192 |

CLASSIFICATION
FILE VIEW

| CLASS | OBJECTS | % OBJECTS | MEAN AREA | MEAN DIA. MEAN |
|---|---|---|---|---|
| 1 | 38 | 19.7911666 | 7.0580130 | 3.1523876 |
| 2 | 39 | 20.31250 | 13.186250 | 4.3244815 |
| 3 | 51 | 26.562498 | 18.550932 | 5.0418862 |
| 4 | 32 | 16.666666 | 24.183006 | 5.6668825 |
| 5 | 11 | 5.7291665 | 29.527105 | 5.9018874 |
| 6 | 6 | 3.1250 | 34.960918 | 6.6136565 |
| 7 | 7 | 3.6458333 | 40.687653 | 7.7858882 |
| 8 | 4 | 2.0833333 | 47.058826 | 8.4272184 |
| 9 | 2 | 1.0416666 | 51.364864 | 7.6277862 |
| 10 | 1 | .52083331 | 58.349068 | 11.660216 |

Fig. 6D.

FIG. 7A.   2101L INNER
FIG. 7B.   2101L INNER
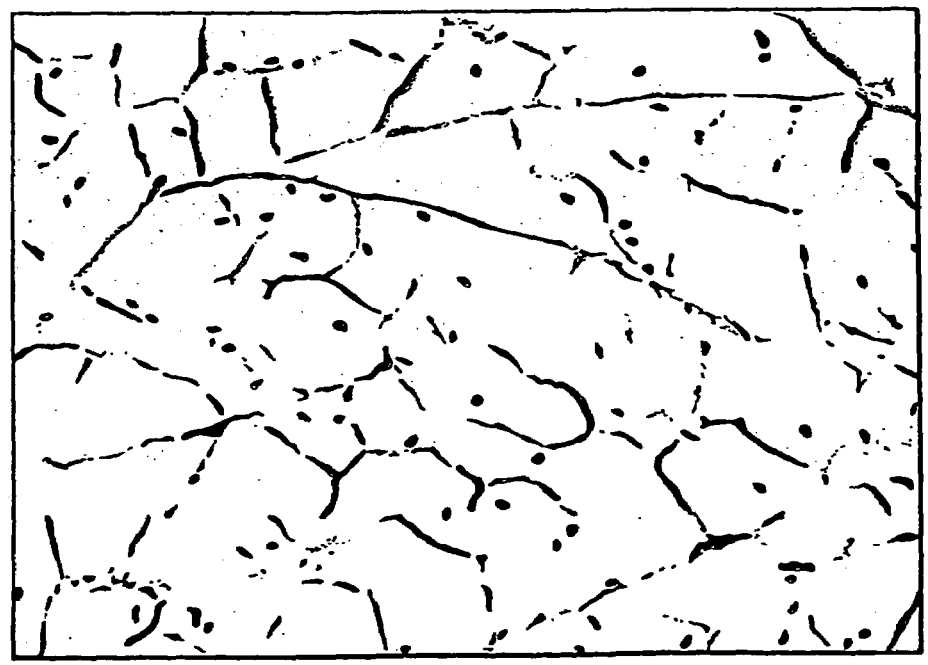

Fig. 7C.

| STATS | AREA | DIAMETER (MEAN) | PER-AREA |
|---|---|---|---|
| MIN | 4.3060360 | 2.3132174 | .00002278 |
| (OBJ. #) | 16 | 202 | 239 |
| MAX | 38.754326 | 9.5076313 | .00020507 |
| (OBJ. #) | 46 | 46 | 46 |
| RANGE | 34.448288 | 7.1944141 | .00018229 |
| MEAN | 12.421543 | 4.1032901 | .00006573 |
| STD. DEV | 6.7874541 | 1.2506217 | .00003591 |
| SUM | 2061.9761 | 681.14618 | .01091145 |
| SAMPLES | 166 | 166 | 166 |

CLASSIFICATION

FILE VIEW

| CLASS | OBJECTS | %OBJECTS | MEAN AREA |
|---|---|---|---|
| 1 | 80 | 48.192772 | 7.3433294 |
| 2 | 48 | 28.915663 | 12.982186 |
| 3 | 21 | 12.650602 | 17.868584 |
| 4 | 8 | 4.8192773 | 23.606304 |
| 5 | 7 | 4.2168674 | 30.318008 |
| 6 | 1 | .60240966 | 36.293732 |
| 7 | 1 | .60240966 | 38.754326 |
| 8 | 0 | 0 | 0 |
| 9 | 0 | 0 | 0 |
| 10 | 0 | 0 | 0 |

Fig. 7D.

FIG. 8A.  1400L INNER
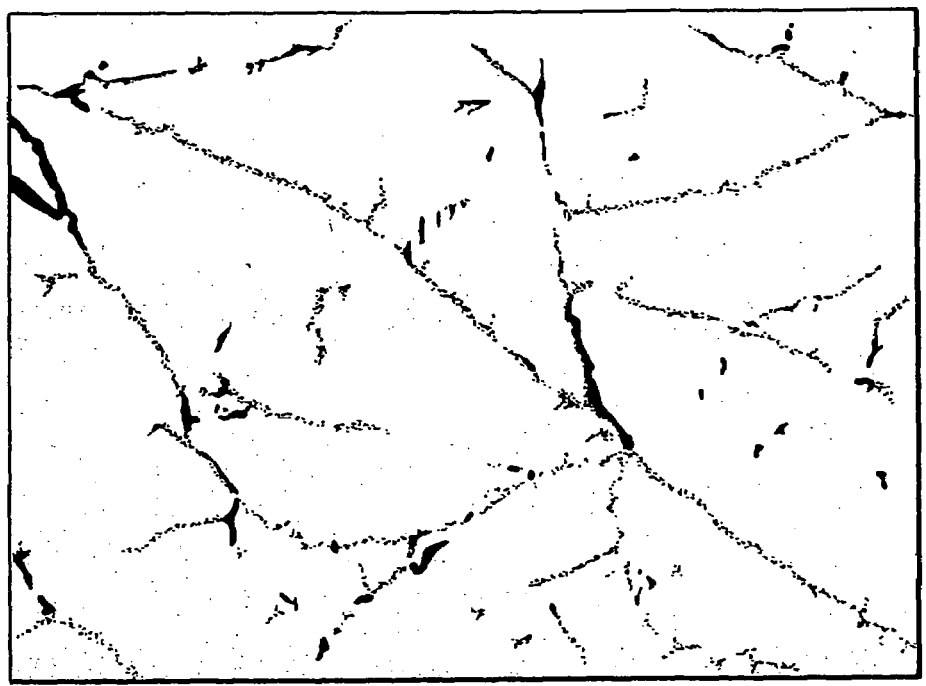
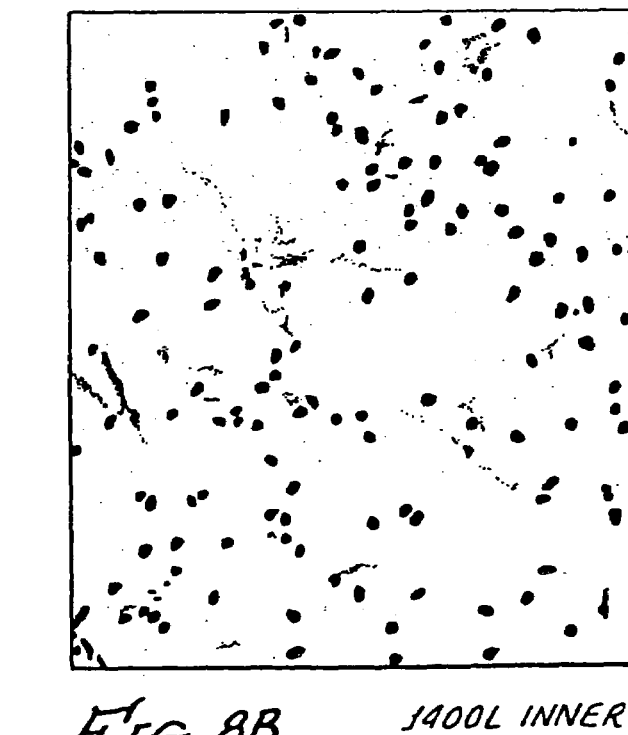
FIG. 8B.  1400L INNER

Fig. 8C.

| STATS | AREA | DIAMETER (MEAN) | PER-AREA |
|---|---|---|---|
| MIN | 4.3060365 | 2.3132176 | .00002278 |
| (OBJ. #) | 120 | 165 | 120 |
| MAX | 102.72973 | 13.133185 | .00054361 |
| (OBJ. #) | 145 | 239 | 145 |
| RANGE | 98.423691 | 10.817967 | .00052083 |
| MEAN | 18.054852 | 4.7163148 | .00009554 |
| STD. DEV | 18.469315 | 1.5011599 | .00006598 |
| SUM | 6698.3501 | 1749.7528 | .03544595 |
| SAMPLES | 371 | 371 | 371 |

Fig. 8D.

CLASSIFICATION

FILE VIEW

| CLASS | OBJECTS | % OBJECTS | MEAN AREA | MEAN DIA [MEAN] |
|---|---|---|---|---|
| 1 | 93 | 25.067385 | 7.0642791 | 3.1215079 |
| 2 | 96 | 25.876011 | 13.059081 | 4.2343669 |
| 3 | 84 | 22.641508 | 18.183481 | 4.9487801 |
| 4 | 51 | 13.746631 | 23.761599 | 5.5594616 |
| 5 | 11 | 2.9649594 | 29.471184 | 6.0824142 |
| 6 | 8 | 2.1563342 | 35.909267 | 6.8700128 |
| 7 | 11 | 2.9649594 | 41.662304 | 7.2421188 |
| 8 | 9 | 2.4258759 | 46.546204 | 7.9324665 |
| 9 | 2 | .53908354 | 53.210308 | 8.4140301 |
| 10 | 2 | .53908354 | 57.208771 | 9.2979317 |

TX00045 MALE RAT INJECTED GASTROCNEMIUS

TX00045 MALE RAT GASTROCNEMIUS

NUCLEI DENSITY AND NUCLEI AREA METHODS FOR DETERMINING EFFECTS OF A BOTULINUM TOXIN ON MUSCLES

CROSS REFERENCE TO RELATED APPLICATIONS

This application is a continuation-in-part of U.S. application Ser. No. 10/208,165, filed Jul. 29, 2002 now U.S. Pat. No. 6,984,375, which claims the benefit of provisional application Ser. No. 60/309,988, filed Aug. 3, 2001, the contents of which in their entireties are hereby incorporated by reference.

BACKGROUND

The present invention is directed to methods for determining the effects of toxins, for example Clostridial neurotoxins. In particular, the present invention is directed to methods for determining the potency of a Clostridial neurotoxin, such as a botulinum toxin, and to distinguish two or more Clostridial neurotoxins.

Botulinum Toxin

The genus *Clostridium* has more than one hundred and twenty seven species, grouped according to their morphology and functions. Certain species produce neurotoxins which reduce or inhibit neuronal activity. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex) is a $LD_{50}$ in mice (i.e. 1 unit). An $LD_{50}$ refers to a lethal dose of botulinum toxin in which fifty percent of a population of mice that receive an intraperitoneal injection of botulinum toxin are killed by the toxin. A purified neurotoxin complex of botulinum toxin type A is available from Allergan, Inc., of Irvine, Calif. under the tradename BOTOX® in 100 unit vials. One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven botulinum neurotoxins have been characterized, these being respectively botulinum neurotoxin serotypes A, B, $C_1$, D, E, F and G each of which is distinguished by neutralization with type-specific antibodies. The different serotypes of botulinum toxin can vary in the animal species that they affect and in the severity and duration of the paralysis they evoke. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Botulinum toxins have been used in clinical settings for the treatment of neuromuscular disorders characterized by hyperactive skeletal muscles. A botulinum toxin type A complex (BOTOX®) has been approved by the U.S. Food and Drug Administration for the treatment of blepharospasm, strabismus and hemifacial spasm, cervical dystonia and treatment of glabellar wrinkles. A type B botulinum toxin (MYOBLOC™) has also been approved by the FDA for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within a day or a few hours after injection. The typical duration of symptomatic relief from a single intramuscular injection of botulinum toxin type A averages about three to four months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem, J* 1;339 (pt 1):159-65:1999, and *Mov Disord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51 (2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373-1412 at 1393; Bigalke H., et al., *Botulinum A Neurotoxin Inhibits Non-Cholinergic Synaptic Transmission in Mouse Spinal Cord Neurons in Culture*, Brain Research 360;318-324:1985; Habermann E., *Inhibition by Tetanus and Botulinum A Toxin of the release of [³H]Noradrenaline and [³H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56;80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1$-$2 \times 10^8$ $LD_{50}$ U/mg or greater; purified botulinum toxin type B with an approximately 156 kD molecular weight with a specific potency of $1$-$2 \times 10^8$ $LD_{50}$ U/mg or greater, and; purified botulinum toxin type F with an approximately 155 kD molecular weight with a specific potency of $1$-$2 \times 10^7$ $LD_{50}$ U/mg or greater.

Botulinum toxins and/or botulinum toxin complexes can be obtained from Allergan Inc (Irvine, Calif.), Ipsen Beaufour (France), Elan Pharmaceuticals (Ireland), List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Though somewhat labile, pure botulinum toxin can be used to prepare a pharmaceutical composition and like the botulinum toxin complexes, such as the toxin type A complex, is susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependent, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein.

The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about four weeks. *Dermatol Surg* Jan. 22, 1996 (1):39-43.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
 (a) flexor digitorum profundus: 7.5 U to 30 U
 (b) flexor digitorum sublimus: 7.5 U to 30 U
 (c) flexor carpi ulnaris: 10 U to 40 U
 (d) flexor carpi radialis: 15 U to 60 U
 (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patient's with Parkinson's disease, although it has been reported that results have not been impressive. Marjama-Jyons, J., et al., *Tremor-Predominant Parkinson's Disease*, Drugs & Aging 16(4);273-278: 2000.

It is known that botulinum toxin type A can have an efficacy for up to 12 months (*European J. Neurology* 6 (Supp 4): S111-S1150:1999), and in some circumstances for as long as 27 months. The Laryngoscope 109:1344-1346:1999. However, the usual duration of an intramuscular injection of Botox® is typically about 3 to 4 months. The success of botulinum toxin type A to treat a variety of clinical conditions has led to interest in other botulinum toxin serotypes. See e.g. *Eur J Neurol* November 1999;6(Suppl 4):S3-S10.

Another type of botulinum toxin type A is available under the tradename DYSPORT® (Ipsen, Inc., Mass.). DYSPORT® is produced by a different strain of *Clostridium botulinum* than BOTOX®. When used as a therapeutic agent, it has been observed that DYSPORT® has a lower potency than BOTOX®.

The tetanus neurotoxin acts mainly in the central nervous system, while botulinum neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

Botulinum Toxin Lethality Assay

The botulinum toxin lethality assay involves the injection of a botulinum toxin composition intraperitoneally into a mouse. For example, the assay may include injecting intraperitoneally (IP) a desired amount of BOTOX® or DYSPORT® into a mouse. Several days after the injection, the injected mice are assessed for mortality. The potency of the product is related to the amount of botulinum toxin that is required to kill 50% of the injected mice ($LD_{50}$).

Contrary to general belief, the mouse unit (i.e., the amount of botulinum toxin that equals the $LD_{50}$) is not a standardized unit. It is well documented that the assay to determine the potency of botulinum toxin type A in mouse $LD_{50}$ units is prone to significant inter-laboratory variability (Schantz and Kautter, *J Ass of Anal Chem* 1978, 61:96-99). One study designed to standardize a Botulinum type A toxin assay involved 11 different laboratories (Sesardic et al, *Pharacol Toxico* 1996, 78:283-288). In this study there was found to be up to a 10-fold difference in results. This variability in mouse $LD_{50}$ is not unique to assays involving botulinum toxin. In fact, because of the variability of this assay, a number of regulatory agencies have abandoned requiring the routine use of $LD_{50}$ for toxicity testing for a number of chemicals, solvents, cosmetics and drugs (Pearce et al, *Toxicol App Pharm* 1994, 128:69-77; U.S. Pat. Nos. 5,401,243 and 5,183,462,).

In addition, although BOTOX® and DYSPORT® are both botulinum toxin type A-containing compositions, BOTOX® has a greater potency than DYSPORT® when therapeutically assessed. However, when measuring the potency of BOTOX® and DYSPORT® using the lethality assay described above, BOTOX® and DYSPORT® exhibit similar potencies.

The expanding medical importance of botulinum toxins has increased the need for, and placed a premium on, the precise analysis of biological activity contained in preparations of botulinum toxin type A for both clinical use and laboratory investigation.

It would be advantageous to provide a more precise measurement of toxin activity, for example toxin potency, which may be more clinically relevant than the existing lethality assay. This invention provides for a better method of determining potency of a toxin relative to the existing lethality assay.

SUMMARY

The present methods may be effective in determining the potency of a Clostridial neurotoxin, such as a botulinum toxin, at one or more therapeutically relevant sites. For example, the amount of change in muscle weight and fiber diameter of a muscle which is injected with a Clostridial neurotoxin will demonstrate the activity and potency of the neurotoxin at a site that is often used in neurotoxin therapy. In other words, the present methods relate to quantifying the amount or degree of muscle atrophy in a muscle that was administered a Clostridial neurotoxin in order to determine the potency of the Clostridial neurotoxin. In addition, the present methods provide the ability to distinguish between two or more Clostridial neurotoxins based on differences in potency at such therapeutic sites.

The present methods may include quantitating and defining the effects of the toxins in terms of "potency". Additionally, the present methods include determining the extent of atrophy cause by the toxins.

In one embodiment, a method for determining the potency of a Clostridial neurotoxin comprises the steps of administering a Clostridial neurotoxin to a muscle of an animal; and quantifying an amount of muscle atrophy in the muscle that was administered the Clostridial neurotoxin. The amount of muscle atrophy correlates to the potency of the Clostridial neurotoxin.

In another embodiment, a method for determining the potency of a Clostridial neurotoxin comprises the steps of administering a Clostridial neurotoxin to a muscle of an animal to provide a neurotoxic effect on the muscle; removing the muscle from the animal at a time when the neurotoxic effect has been achieved; and determining an amount of muscle atrophy of the muscle that was administered the Clostridial neurotoxin, thereby determining the potency of the Clostridial neurotoxin.

In yet another embodiment, a method for distinguishing a first Clostridial neurotoxin from a second Clostridial neurotoxin comprises the steps of quantifying muscle atrophy of a first muscle in which the first Clostridial neurotoxin has been administered to determine potency of the first Clostridial neurotoxin. Quantifying muscle atrophy of a second muscle in which the second Clostridial neurotoxin has been administered to determine the potency of the second Clostridial neurotoxin. And, comparing the potency of the first Clostridial neurotoxin to the potency of the second Clostridial neurotoxin. A difference in potency is effective in distinguishing the first Clostridial neurotoxin from the second Clostridial neurotoxin.

In a further embodiment, a method for distinguishing a potency of each of at least two Clostridial neurotoxins comprises the steps of administering a first Clostridial neurotoxin to a first muscle of a first animal; administering a second Clostridial neurotoxin to a second muscle of a second animal, wherein the second muscle is the same type of muscle as the first muscle; and comparing the weight of the first muscle to the weight of the second muscle. A difference in weight between the first muscle and the second muscle correlates to a difference in potency of the first Clostridial neurotoxin and the second Clostridial neurotoxin.

As discussed herein, the methods may be practiced utilizing a botulinum toxin selected from the group consisting of botulinum toxin types A, B, C, D, E, F, and G. The neurotoxins are administered to muscles, such as leg muscles, of animals, such as rodents.

Thus, the present methods provide improvements and advantages over the existing Lethality Assay described herein.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DRAWINGS

FIGS. 5, 6, 7 and 8 show a computer recognition and analysis of nuclei on muscle slides. The muscles of FIGS. 5 and 7 are not treated with botulinum toxin. The muscles of FIGS. 6 and 8 are treated with botulinum toxin.

Figure 9:
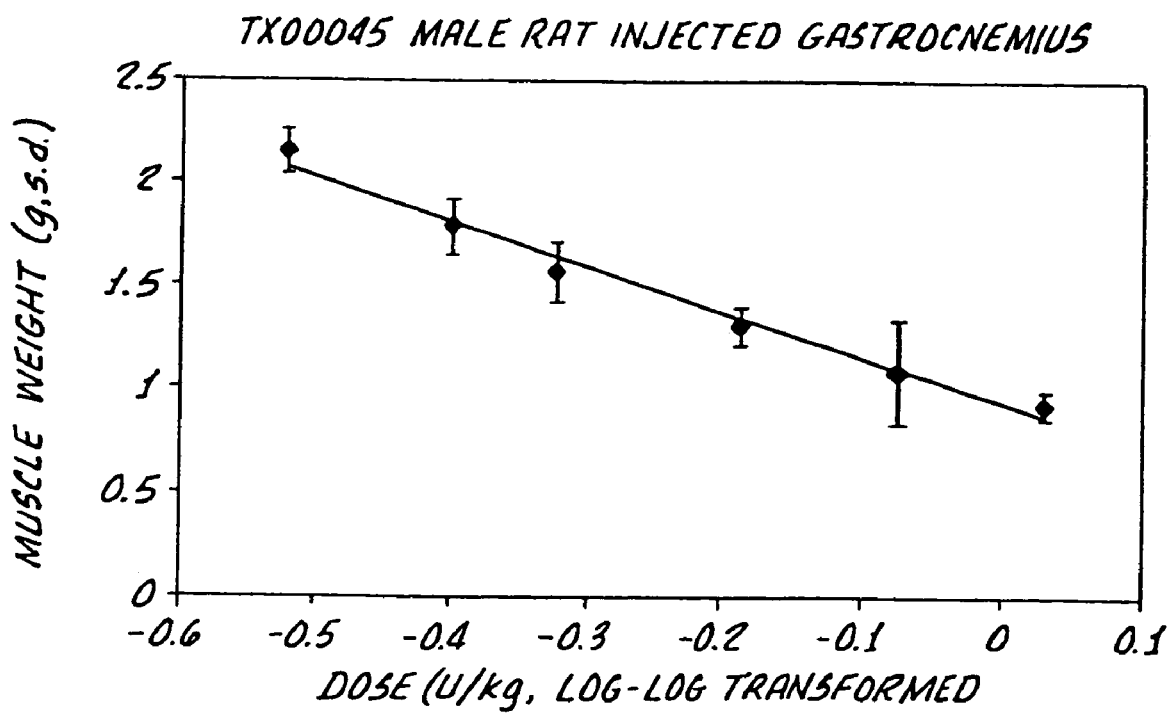

FIG. 9 shows the relationship between muscle weight and dose of botulinum toxin injected.

Figure 10:
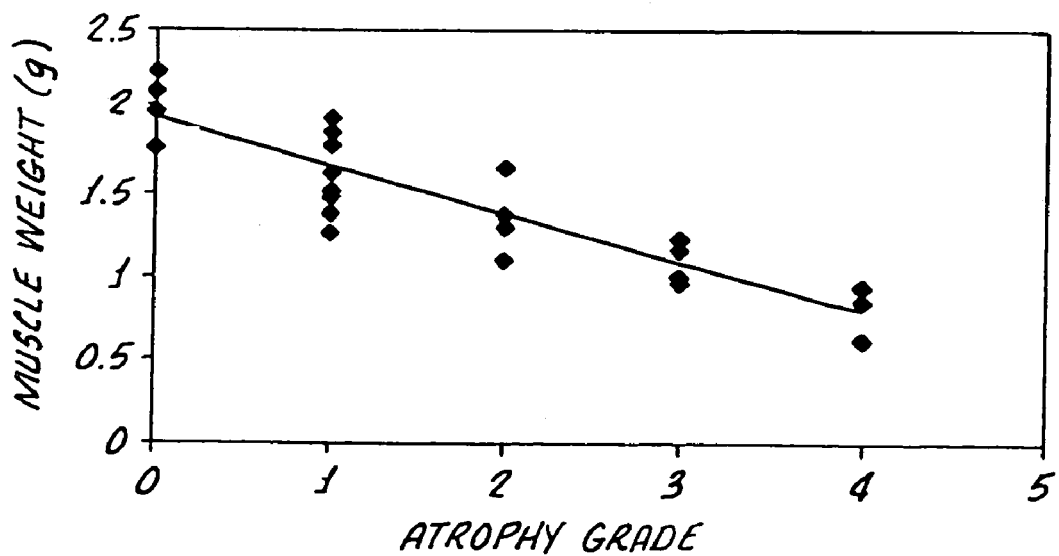

FIG. 10 shows the relationship of muscle weight and atrophy grade.

Figure 11:
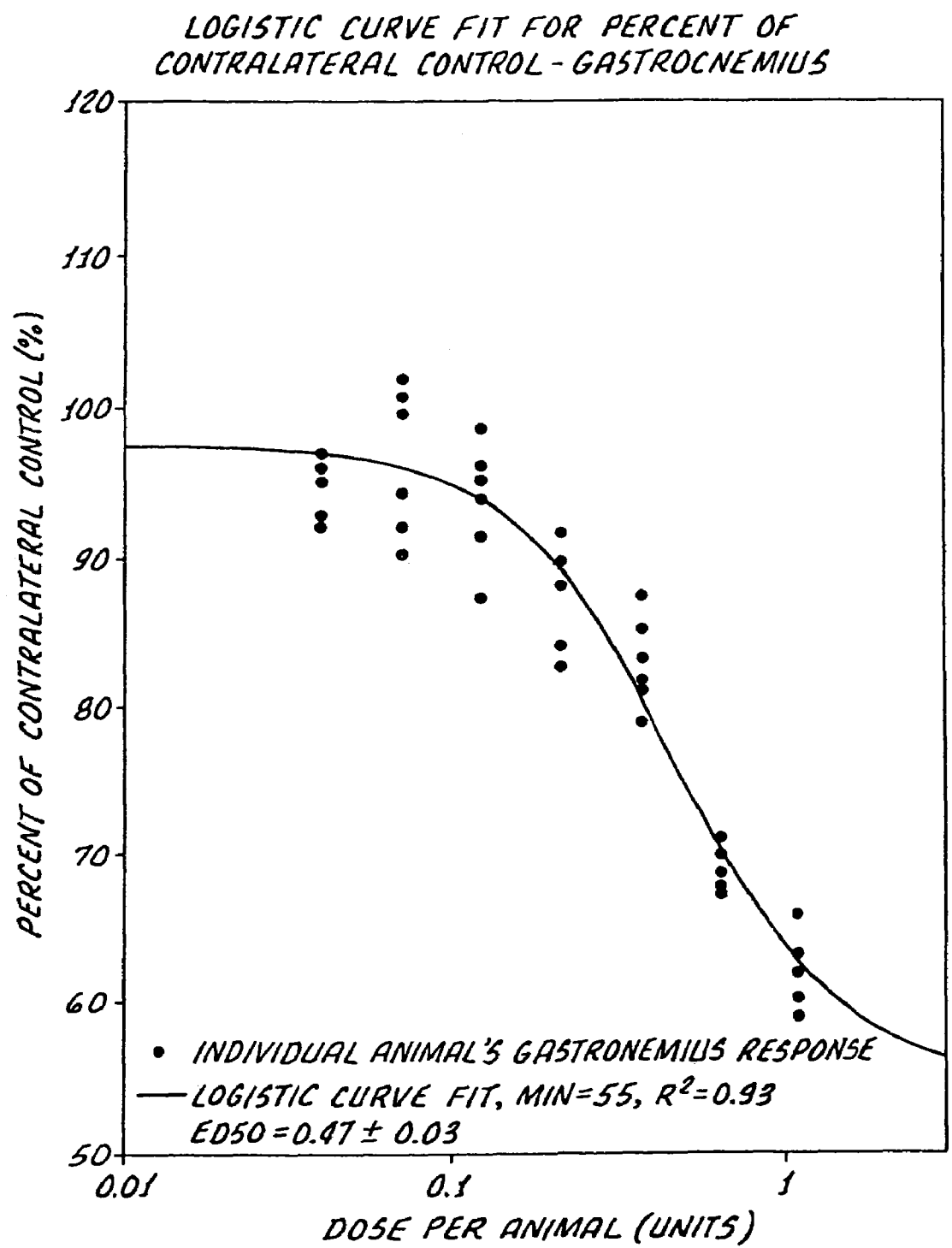

FIG. 11 is a graph which shows the result of an experiment where the left gastrocnemius muscle of different rats was injected with varying amounts of a botulinum toxin type A. The y axis shows the ratio (as a percent) of the weight of the toxin injected left gastrocnemius muscle of the rat to the weight of the uninjected right gastrocnemius muscle of the same rat. The x axis shows the amount in units of the botulinum toxin type A that was injected into the left gastrocnemius muscle.

Figure 12:
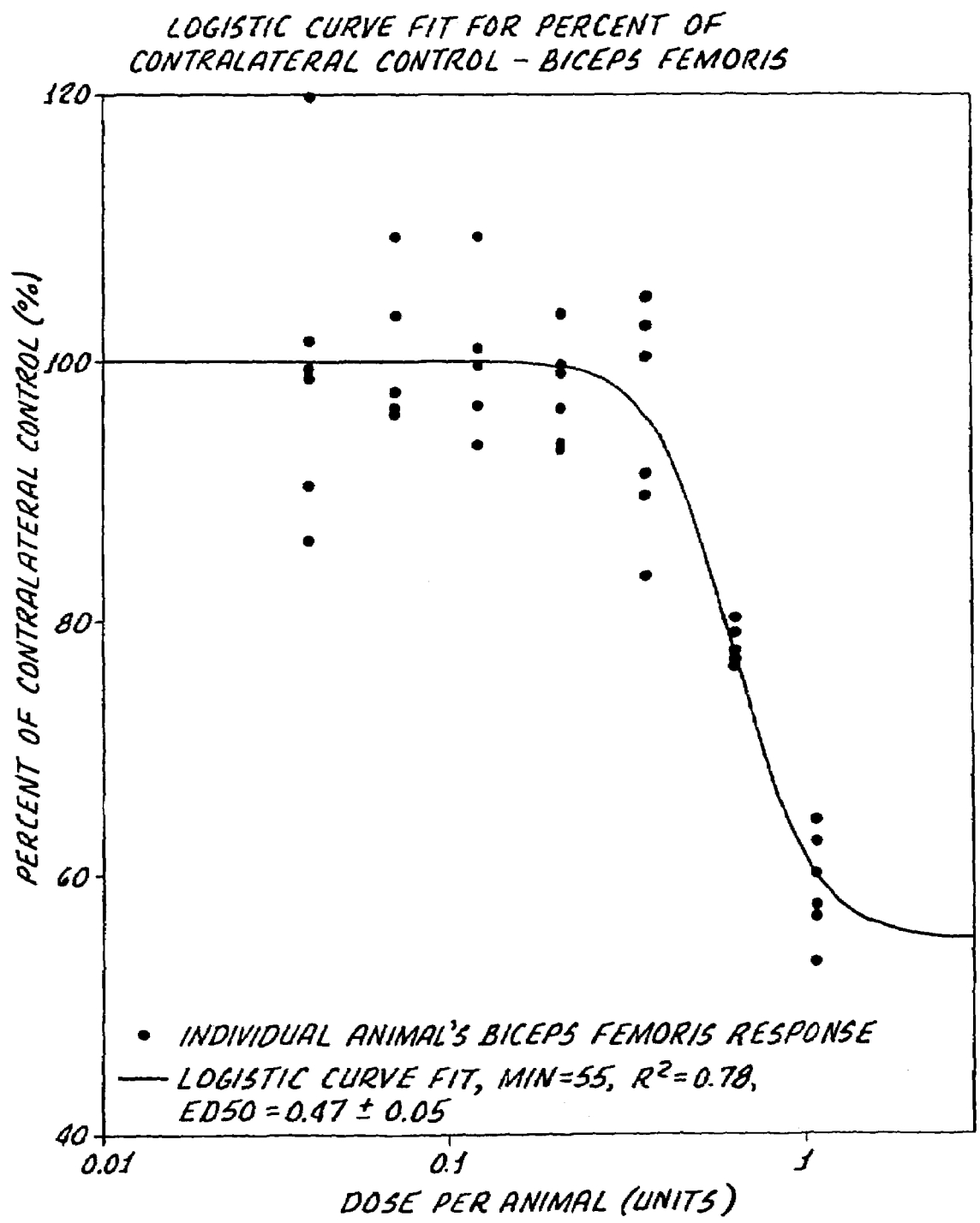

FIG. 12 is a graph which shows the result of an experiment where the left gastrocnemius muscle of different rats was injected with varying amounts of a botulinum toxin type A. The y axis shows the ratio (as a percent) of the weight of the uninjected left biceps femoris muscle (which is adjacent to the toxin injected left gastrocnemius muscle of the rat) to the weight of the uninjected right biceps femoris muscle of the same rat. The x axis shows the amount in units of the botulinum toxin type A that was injected into the left gastrocnemius muscle.

Figure 13:
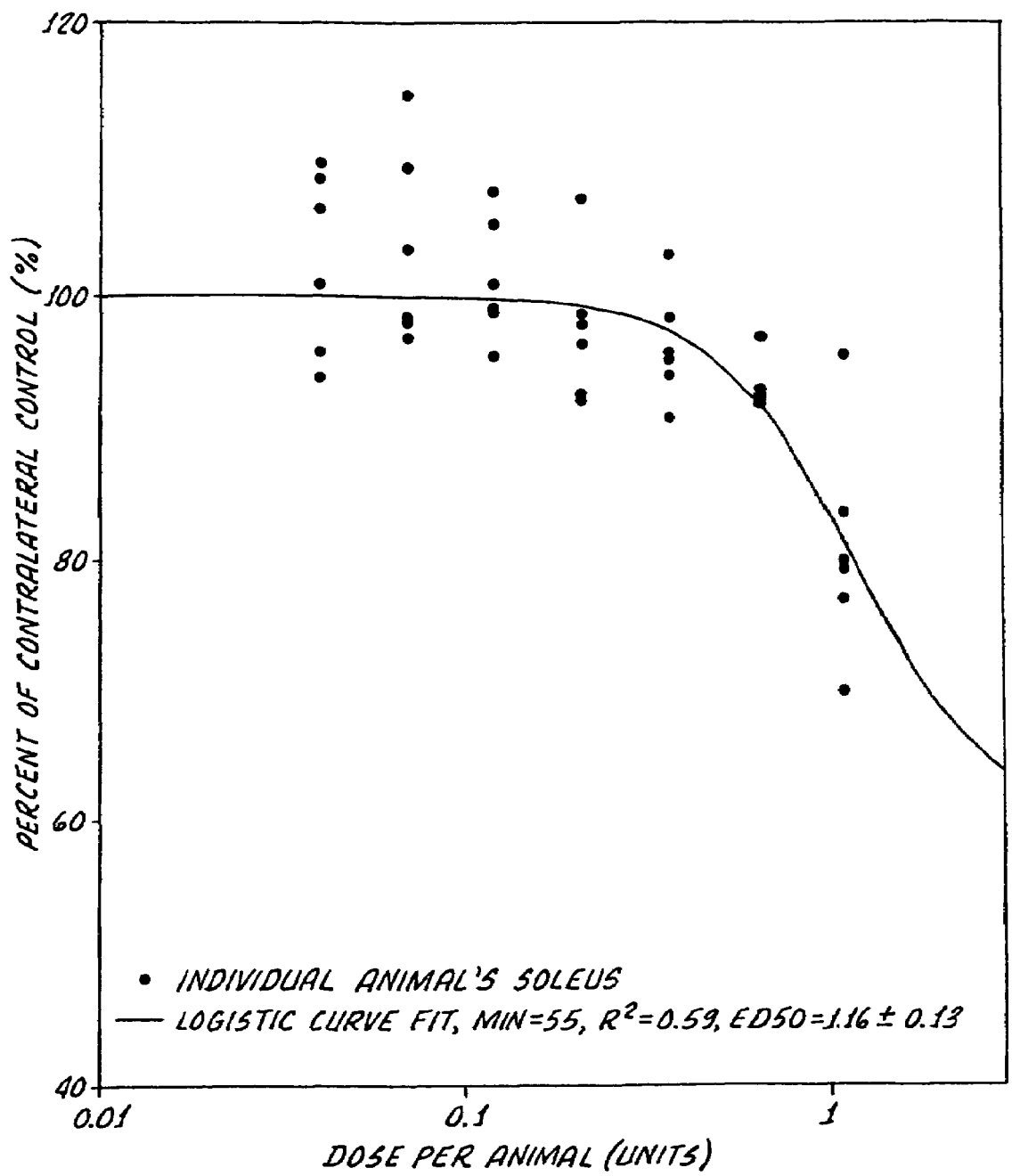

FIG. 13 is a graph which shows the result of an experiment where the left gastrocnemius muscle of different rats was injected with varying amounts of a botulinum toxin type A. The y axis shows the ratio (as a percent) of the weight of the uninjected left soleus muscle (which is adjacent to the toxin injected left gastrocnemius muscle of the rat) to the weight of the uninjected right soleus muscle of the same rat. The x axis shows the amount in units of the botulinum toxin type A that was injected into the left gastrocnemius muscle.

Figure 14:
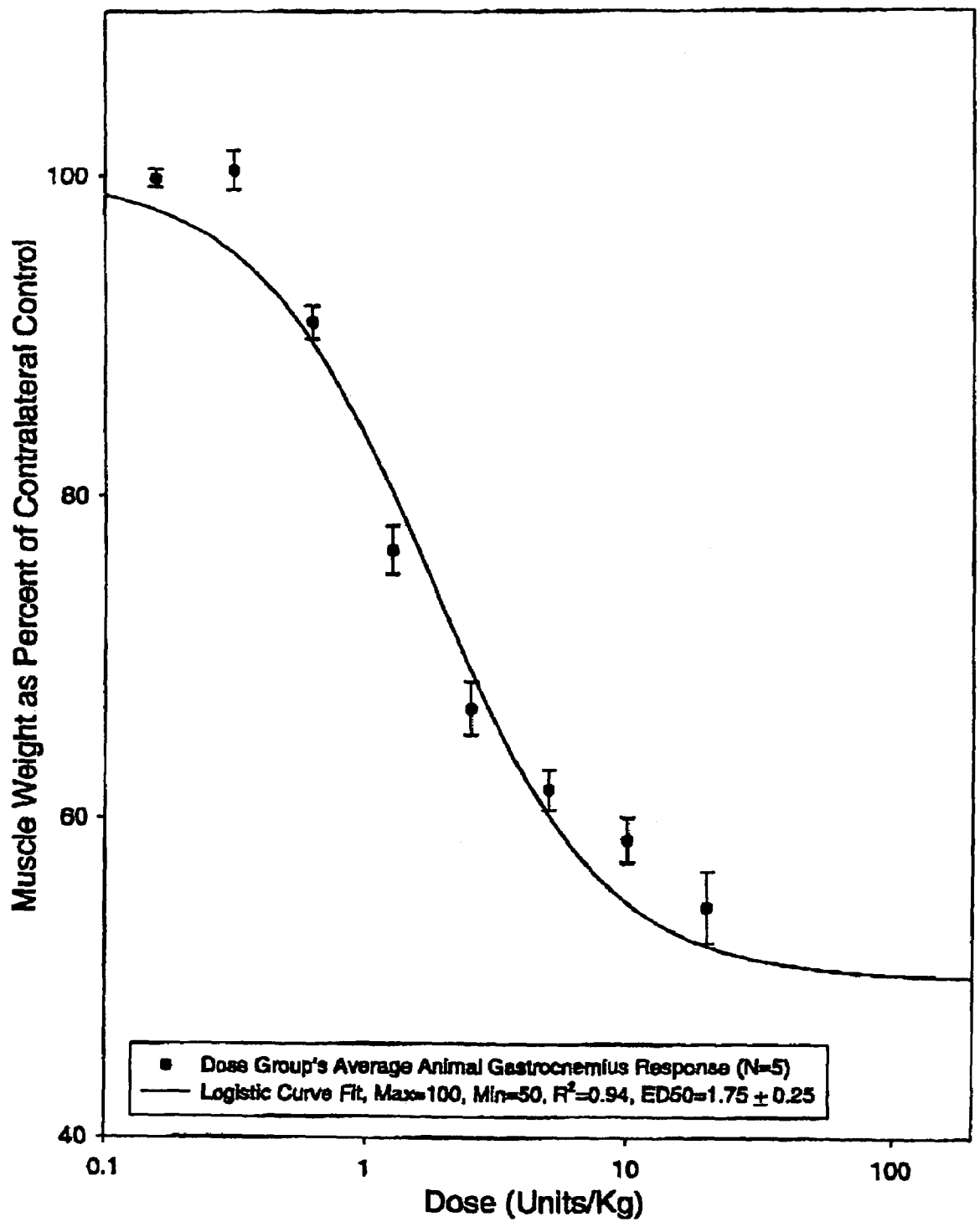

FIG. 14 is a graph which shows the result of an experiment where the left gastrocnemius muscle of a plurality of rats was injected with varying amounts of BOTOX®. The y axis shows the muscle weight of the injected muscles as a percent of the contralateral control muscle. The x axis shows the dosage or dose of botulinum toxin type A that was injected in the muscle.

Figure 15:
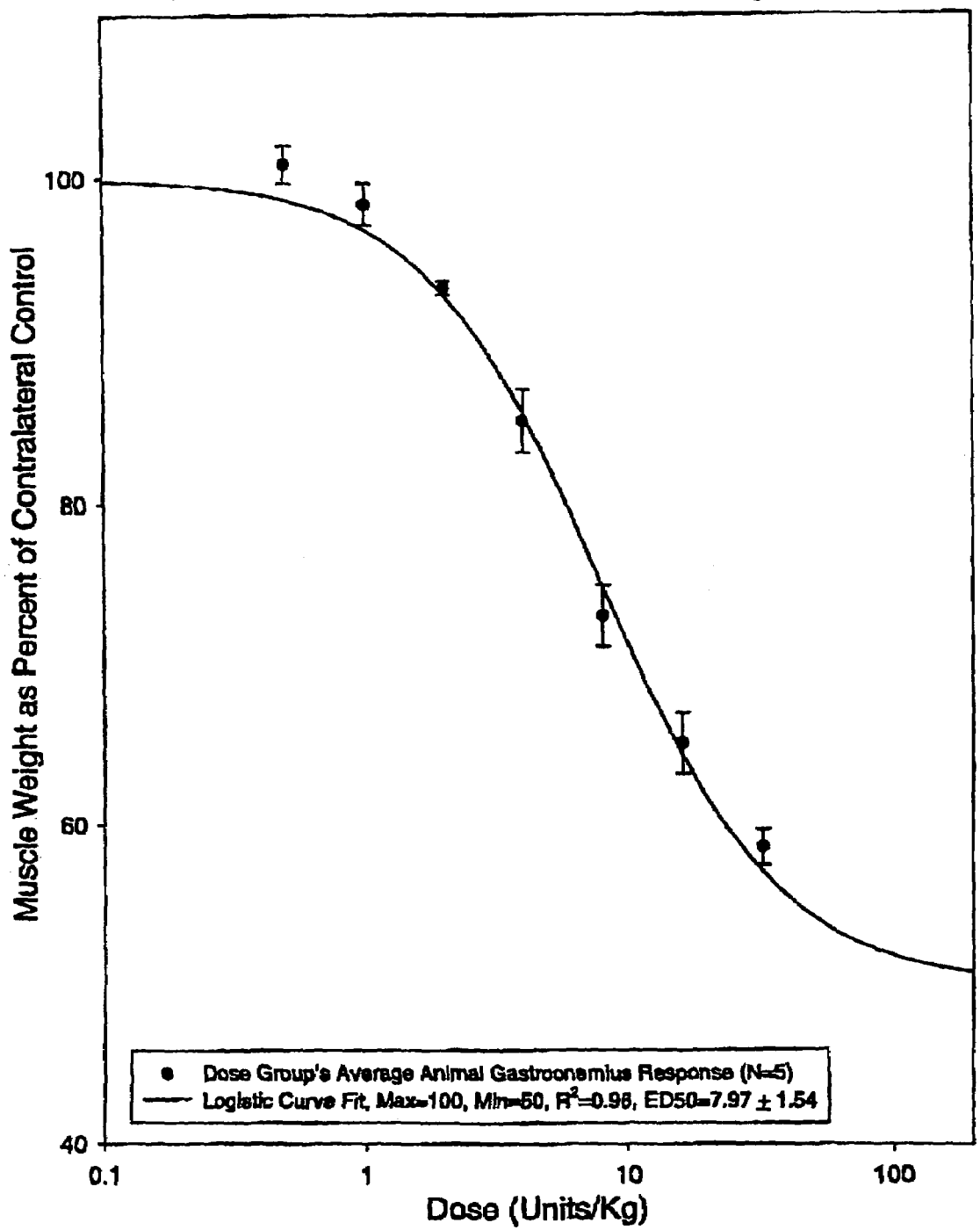

FIG. 15 is a graph which shows the result of an experiment where the left gastrocnemius muscle of a plurality of rats was injected with varying amounts of DYSPORT®. The y axis shows the muscle weight of the injected muscles as a percent of the contralateral control muscle. The x axis shows the dosage or dose of botulinum toxin type A that was injected in the muscle.

DEFINITIONS

"Potency" refers to a measure of a mass or amount of a certain chemical, e.g. a neurotoxin, to induce a certain degree of physiological or chemical effect. For example, potency of a botulinum toxin means the extent of or the duration of inhibition of acetylcholine release from a target tissue. Alternatively, a potency of a botulinum toxin means the extent that a certain dose of toxin causes a certain nuclear index changes, or a degree or extent of muscle atrophy.

"Atrophy" refers to a reduction in muscle mass. The degree of muscle atrophy can be measured by a change in muscle weight, circumference and/or length, and a change in muscle fiber diameter.

"Nuclear index" means number of nuclei per area of muscle (nuclei density), the sum of the area of the individual nuclei within a field (nuclei area), and/or the level of electrically coupled factors.

"Electrically coupled factors" may be proteins (for example, transcription factors) or nucleic acid sequences [e.g. mRNA] of MyoD, Myogenin, Myr-5, MRF4, sTnI, and/or tTnI.

"Muscle Weight" is the mass of the muscle.

"Atrophy grade" is the percentage of atrophy of a muscle fiber, relative to an analogous control muscle fiber, which may be determine via visual inspection. Each "grade" corresponds to about 25% reduction in muscle mass relative to the control.

DESCRIPTION

Our invention encompasses a method for determining an effect, such as a potency, of a Clostridial neurotoxin. The present invention also encompasses a method for distinguishing two or more Clostridial neurotoxins by comparing the potency of each of the two or more Clostridial neurotoxins. The present methods comprise the step of administering a Clostridial neurotoxin to a muscle of an animal, such as a mammal, and quantifying an amount or degree of muscle atrophy of the muscle in which the Clostridial neurotoxin was administered. For example, the quantifying may include determining a nuclear index of an injected muscle, or may include determining the weight or size of an injected muscle, as discussed herein.

The Clostridial neurotoxin used in the present methods can be any neurotoxin obtained or from Clostridial bacteria, including without limitation, Clostridial bacteria selected from the group consisting of Clostridial beratti, Clostridia butyricum, Clostridial tetani and Clostridial botulinum. In certain embodiments, including the illustrated embodiments, the Clostridial neurotoxin is a botulinum toxin. The botulinum toxin can be selected from the group consisting of botulinum toxin types A, B, C, D, E, F, G and mixtures thereof. In at least one embodiment, a Clostridial neurotoxin used in the present methods is botulinum toxin type A. With respect to the present methods, the Clostridial neurotoxin is an agent that can inhibit or reduce neuronal activity. For example, the agent may inhibit neurotransmitter release from a neuron, or the agent may reduce action potential discharge of a neuron. Suitable Clostridial neurotoxins can be obtained commercially, or by culturing different strains of Clostridial bacterium using conventional methods known to persons of ordinary skill in the art. Clostridial neurotoxins may be identified for their neurotoxic effects using conventional methods known to persons of ordinary skill in the art, such as by monitoring the effect of the neurotoxins on neurotransmitter release using electrophysiological recording methods, such as patch clamp or intracellular electrophysiological recordings.

An effect of a Clostridial neurotoxin can be determined by determining a potency or diffusion of the neurotoxin. Such a determination can be carried out by determining the nuclear index which comprises measuring nuclei density. The step of determining the nuclear index can comprise measuring nuclei area. Additionally, the step of determining the nuclear index comprises measuring the nuclei density and nuclei area. The step of determining the nuclear index can comprise measuring the level of electrically coupled factors. The step of determining the nuclear index can comprise measuring the level of electrically coupled factors and nuclei density. The step of determining the nuclear index can comprise measuring the level of electrically coupled factors and nuclei area.

Additionally, the step of determining the nuclear index can comprise measuring the level of electrically coupled factors, nuclei density, and nuclei area. The electrically coupled factors can comprise proteins. The electrically coupled factors can comprise nucleic acid sequences. The electrically coupled factors can comprise the mRNAs of MyoD, Myogenin, Myr-5, MRF4, sTnI, tTnI.

The present invention also provides a method for determining muscle atrophy induced by the administration of a Clostridium neurotoxin, the method comprises the step of comparing a nuclear index of the muscle injected with Clostridial neurotoxin to that of a muscle which is not injected with Clostridial neurotoxin. The nuclear index can be measurement of the level of electrically coupled factors, nuclei density, and nuclei area.

A method for determining an effect of a Clostridial neurotoxin, may comprise the step of administering the Clostridial neurotoxin to a muscle of a mammal, and determining an amount or degree atrophy of the muscle. The effect of a Clostridial neurotoxin can be determined by determining a potency of the neurotoxin. The step of determining atrophy can comprise measuring a reduction in muscle mass of either the muscle injected with the toxin or of an adjacent muscle.

A method for determining an effect of a Clostridial neurotoxin, may comprise the step of administering the Clostridial neurotoxin to a muscle of a mammal, and determining an amount or degree of atrophy of the muscle by comparing a muscle mass of the muscle injected with a Clostridial neurotoxin to that of a muscle which is not injected with a Clostridial neurotoxin.

I. Methods of Determining the Potency of a Toxin

In one embodiment, a method for determining an effect of a Clostridial neurotoxin comprises the steps of administering, such as by injecting, the toxin to a muscle of a mammal and determining the nuclear index of the injected muscle. The effect of the neurotoxin may be defined by its potency. In one embodiment, the present invention provides for a method of determining the potency of a Clostridial neurotoxin on a muscle. "Mammals" as used herein include, for example, human beings, rats, rabbits, mice and dogs.

A step of determining the nuclear index includes measuring the number of nuclei per area of tissue, measuring the sum of the individual area of the nuclei over an area of tissue, and/or measuring the level of electrically coupled factors. Examples of electrically coupled factors include mRNAs of MyoD, Myogenin, Myr-5, MRF4, sTnI and/or tTnI. See Voytik et al., Developmental Dynamics 198:214-224 (1993).

It has been discovered that the number and size of nuclei, in particular the sarcolemma nuclei, increases with an increasing dose of toxin, for example botulinum toxin type A, that is administered to a muscle. Also, the level of electrically coupled factors in the muscle changes, for example increases or decreases, with an increasing dose of toxin. As such, a dose response curve may be constructed to determine a potency of a toxin. The potency as determined by this method is termed $ED_{50}$ (effective dose at 50%). It is believed that the potency as determined by this method is more accurate and more reliable than the traditional $LD_{50}$, as described above.

Figure 1:
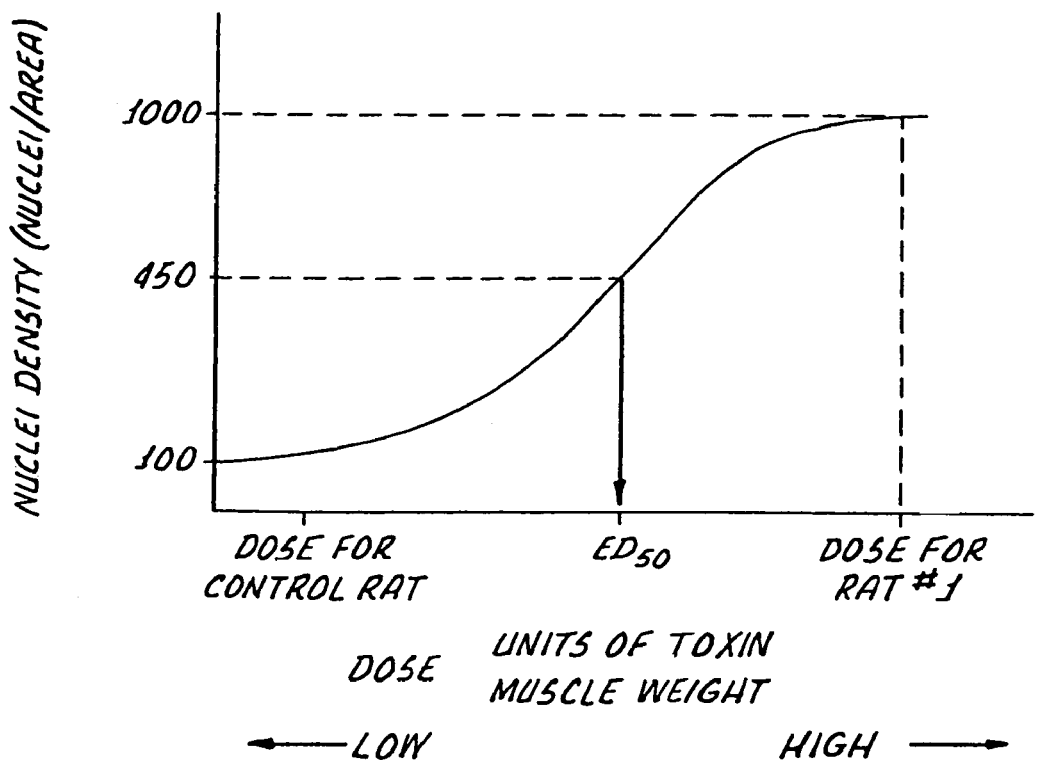
FIG. 1 illustrates a sample dose response curve constructed from plotting the nuclear index against the dose of toxin, for example botulinum toxin.

FIG. 1 shows an exemplary dose response curve constructed from plotting the nuclear density against an increasing dose of toxin, for example botulinum toxin. The $ED_{50}$ is the concentration which corresponds to the halfway point between the lowest and the highest nuclei density. For example, the $ED_{50}$ of FIG. 1 is the dose of botulinum toxin corresponding to 450 nuclei/unit area, which is half of 1000 and 100 nuclei/unit area.

The nuclei area may be plotted against the varying dose of a Clostridial toxin, preferably botulinum toxin, to obtain an $ED_{50}$.

Standard nuclei staining techniques may be employed to identify the nuclei for purposes of counting the number of nuclei or determining the sum of their area. Various non-limiting examples of staining techniques are listed herein below.

After staining the nuclei, the nuclear index, for example the number of nuclei per area of muscle tissue or the sum of the individual nuclei over an area of muscle tissue, may be obtained with an assistance of a computer. Various computer programs known in the art may be employed in accordance with this invention. In one embodiment, these programs are used to direct a computer to recognize certain patterns, preferably that of a nucleus, on a stained muscle slide. After identifying the nuclei, the program will further direct the computer to sort the nuclei according to size or volume and group them into bins of similar sizes or volume. An example of such program which may be used in accordance with this invention includes Image Pro 4.1 (MediaCybernetics, Inc.).

FIG. 5B shows a computer recognition image of the nuclei of a muscle slide. FIG. 5D shows that there are ten bins. Bin #1 has 54 objects (or nuclei) having the mean area of 7.5 um. FIG. 5C shows that there are a total of 106 nuclei. FIG. 6 shows that when an analogous muscle is treated with botulinum toxin, the nuclei are larger, more plump and more numerous. For example, FIG. 6D shows that there are nuclei as large as 58 µm. Furthermore, FIG. 6C shows that the number of nuclei increases to 192. FIG. 7 relates to FIG. 8 as FIG. 5 relates to FIG. 6.

In view of the disclosure herein, the present invention includes a method for determining the potency of a Clostridial neurotoxin.

In certain embodiments, the method for determining the potency of a Clostridial neurotoxin comprises the steps of administering a Clostridial neurotoxin to a muscle of an animal, and quantifying an amount of muscle atrophy of the muscle that was administered the Clostridial neurotoxin. The amount of muscle atrophy correlates to the potency of the Clostridial neurotoxin. For example, a more potent neurotoxin will cause a greater amount of muscle atrophy of a given dosage than a less potent neurotoxin.

The administration of the Clostridial neurotoxin may be accomplished by intramuscularly injecting the neurotoxin into a muscle. However, other modes of administration may also be provided, such as by using a needless syringe, or placing an implant into or near muscle tissue, for example. In the illustrated embodiment, the Clostridial neurotoxin is injected into a gastrocnemius muscle of an animal, for example a rodent, such as a rat.

The quantifying step of the foregoing method may comprise weighing the muscle that was administered the Clostridial neurotoxin. In other embodiments, the quantifying step may comprise determining a nuclear index of the muscle, as described herein, or by determining changes in muscle fiber diameter.

As discussed in more detail in the Examples hereinbelow, the foregoing method may comprise administering multiple different dosages of the Clostridial neurotoxin to a plurality of animals. Each animal will receive a single dosage of the Clostridial neurotoxin. For example, a group of five animals may be administered 2 Units of BOTOX®, a second group of five animals may be administered 5 Units of BOTOX®, a third group of five animals may be administered 20 units of BOTOX®, and the like. By obtaining data from multiple animals receiving different dosages of the Clostridial neurotoxin, it is possible to calculate a dose-response curve for the Clostridial neurotoxin. Thus, the method of the present invention may comprise a step of determining an ED50 of the Clostridial neurotoxin based on the amount of muscle atrophy in each of the plurality of animals. The ED50 can be determined using conventional techniques readily understood by persons of ordinary skill in the art. For example, the muscle atrophy data can be entered into a statistical software program of a computer. Such software is typically provided with one or more curve-fitting models. These models can be used to provide a mathematical description of the muscle atrophy data, from which the ED50 can then be determined.

In another embodiment, a method for determining the potency of a Clostridial neurotoxin comprises the steps of administering a Clostridial neurotoxin to a muscle of an animal to provide a neurotoxic effect to the muscle. The method comprises removing the muscle from the animal at a time when the neurotoxic effect has been achieved. An amount of muscle atrophy of the muscle that was administered the neurotoxin is determined. By determining or quantifying the amount of muscle atrophy, the potency of the Clostridial neurotoxin can be determined.

The Clostridial neurotoxin of the foregoing methods may be a botulinum toxin. For example, the Clostridial neurotoxin may be a botulinum toxin selected from the group consisting of botulinum toxin types A, B, C, D, E, F, and G. In the illustrated embodiment, the Clostridial neurotoxin is botulinum toxin type A.

In the methods described above employing botulinum toxin type A, the dosage of the botulinum toxin type A may be greater than 0 U/kg body weight and less than about 10 U/kg.

The potency may be determined by administering the Clostridial neurotoxin to a leg muscle, such as a gastrocnemius muscle, of a rodent, such as a rat.

When a method comprises a step of removing the muscle from the animal, the muscle is removed after the neurotoxic effects have been achieved. For example, the muscle may be removed about two weeks after administration of the Clostridial neurotoxin to the muscle.

As discussed herein, the muscle atrophy may be determined or quantified by weighing the muscle. Thus, a method in accordance with the foregoing embodiments may comprise a step of comparing the weight of the muscle that was administered the Clostridial neurotoxin to a control muscle or a muscle that was not administered a Clostridial neurotoxin. The control muscle may be the same type of muscle on the contralateral side of the same animal, or it may be the same type of muscle from a different animal. The muscle atrophy may also be determined by measuring muscle fiber diameter, and/or using histopathology techniques, such as nuclear staining, The methods may comprise repeating the steps described above in a plurality of animals. Such steps may be effective in obtaining data which may be used to construct a dose-response curve of the degree of muscle atrophy versus dosages of the Clostridial neurotoxin. Thus, a method may further comprise a step of measuring an ED50 from weight data obtained from the plurality of animals, as described herein.

In another embodiment of the present invention, a method has been discovered for distinguishing a Clostridial neurotoxin from one or more other Clostridial neurotoxins. Unexpectedly, it has been discovered that the present methods provide enhancements in measuring the potency of Clostridial neurotoxins that more closely correlate to therapeutic use of such neurotoxins compared to the conventional lethality assay.

In one embodiment, a method for distinguishing a first Clostridial neurotoxin from a second Clostridial neurotoxin comprises the steps of quantifying muscle atrophy of a first muscle in which the first Clostridial neurotoxin has been administered to determine the potency of the first Clostridial neurotoxin; quantifying muscle atrophy of a second muscle in which the second Clostridial neurotoxin has been administered to determine the potency of the second Clostridial neurotoxin; and comparing the potency of the first Clostridial neurotoxin to the potency of the second Clostridial neurotoxin. The difference in potency between the first and second Clostridial neurotoxin is effective in distinguishing the first Clostridial neurotoxin from the second Clostridial neurotoxin.

In another embodiment, a method for distinguishing a potency of each of at least two Clostridial neurotoxins comprises the steps of administering a first Clostridial neurotoxin to a first muscle of a first animal; and administering a second Clostridial neurotoxin to a second muscle of a second animal. The second muscle is the same type of muscle as the first muscle. The method also comprises a step of comparing the weight of the first muscle to the weight of the second muscle. A difference in the weight between the first muscle and the second muscle correlates to a difference in potency of the first Clostridial neurotoxin and the second Clostridial neurotoxin.

As discussed herein, the administration of the Clostridial neurotoxins to the muscles may be achieved by intramuscular injection, needleless injection, placement of neurotoxin containing implants into or near the muscle, and the like.

The first Clostridial neurotoxin and the second Clostridial neurotoxin used in the methods for distinguishing two or more neurotoxins, described herein, may both be botulinum toxin type A, but each botulinum toxin type A being obtained from different strains of Clostridial bacteria. For example, the first Clostridial neurotoxin may be a botulinum toxin type A, which is publicly available under the trademark BOTOX®, and the second Clostridial neurotoxin may be a botulinum toxin type A, which is publicly available under the trademark DYSPORT®. Alternatively, the first neurotoxin may be a botulinum toxin type B obtained from a first strain of *Clostridium* bacteria, and the second neurotoxin may be a botulinum toxin type B obtained from a second different strain of a *Clostridium* bacteria.

In other embodiments, the first Clostridial neurotoxin and the second Clostridial neurotoxin may be different types of botulinum toxin. For example, either the first or the second Clostridial neurotoxin may be botulinum toxin type A (such as available as BOTOX® or DYSPORT®), and the other Clostridial neurotoxin may be a botulinum toxin selected from the group consisting of botulinum toxin types B, C, D, E, F, and G.

When a botulinum toxin type A is used, the dosage is less than about 70 U/kg (body weight) in certain embodiments. For example, the first Clostridial neurotoxin, such as BOTOX®, may administered at a dosage greater than 0 U/kg and less than about 20 U/kg. The second Clostridial neurotoxin, such as DYSPORT®, may be administered at a dosage between 0 U/kg and about 64 U/kg.

In certain embodiments, the first muscle and the second muscle of the foregoing method are each a gastrocnemius muscle of an animal. In other embodiments, the first and second muscle are rodent muscles, including muscles other than the gastrocnemius. Suitable muscles should be selected for ease of accessibility, ease of administration of the neurotoxin, and ease of analysis, among other things. Selecting a suitable muscle may be achieved using conventional methods known to persons of ordinary skill in the art. Preferably, the muscles are not critical for short-term survival of the animal (such as weeks or months). For example, the heart would not be a suitable muscle to inject in many embodiments of the present methods. Typically, the first muscle and the second muscle are muscles in different animals; however, in certain embodiments, such as when standard dose response curves are already available, the first and second muscles may be in the same animal. For example, the first muscle may be a left gastrocnemius, and the second muscle may be the right gastrocnemius. When the Clostridial neurotoxins are administered to a gastrocnemius muscle, the neurotoxin may be administered to the midbelly area, the lateral head, or a combination thereof. It is to be understood that differences in location may affect the actual potency values that are determined using the methods of the present invention, such as shown in FIG. 13 and FIG. 14. However, such effects in potency are minimized when the first Clostridial neurotoxin and the second Clostridial neurotoxin are administered to the same site in their respective muscles.

After administering the neurotoxins to the muscles, each muscle may be weighed to quantify the degree of muscle atrophy. The weights of the muscles may then be compared to each other, as well as compared to a control muscle. The weight of the muscle is usually determined after the neurotoxin has provided a neurotoxic effect. For example, in rats, the muscles are weighed at about two weeks after the neurotoxins are administered to the muscles. The muscles may be weighed by removing the muscles from the animals and weighing the muscles using conventional techniques known to persons of ordinary skill in the art.

The methods may be repeated in a plurality of animals, as described herein, to obtain a dose response curve for the first Clostridial neurotoxin and the second Clostridial neurotoxin. The data for the dose-response curves may then be used to determine an ED50 for the first Clostridial neurotoxin and the second Clostridial neurotoxin. The differences in ED50 between the first and second neurotoxins correlates to differences in potency of each neurotoxin, and thus, are effective in distinguishing one neurotoxin from another neurotoxin.

Addition details regarding the present methods are provided in the following Examples. The Examples are provided in context with the rest of the present disclosure, and are not to be construed to limit the present invention. The Examples are provided for illustrative purposes to describe certain embodiments of the present methods.

EXAMPLE 1

Determining the Potency of Botulinum Toxin with Nuclei Area

A batch of botulinum toxin type A is prepared by a standard methodology. A serial dilution of the toxin is done by a standard methodology. The stock solution of the toxin is set at an approximate concentration of 50 picograms of botulinum toxin type A/microliter. Five fold dilutions are done with the final serial dilution factors ranging from 1.0 (stock solution) to $1.0 \times 10^{-4}$. In addition, rats, one for each serial dilution, are prepared for a potency assay. 1.0 microliter of each of the nine dilutions is injected into the gastrocnemius muscle of each of the rats as follows:

Rat No. 1, dilution factor=1.0
Rat No. 2, dilution factor=$5.0 \times 10^{-1}$
Rat No. 3, dilution factor=$1.0 \times 10^{-1}$
Rat No. 4, dilution factor=$5.0 \times 10^{-2}$
Rat No. 5, dilution factor=$1.0 \times 10^{-2}$
Rat No. 6, dilution factor=$5.0 \times 10^{-3}$
Rat No. 7, dilution factor=$1.0 \times 10^{-3}$
Rat No. 8, dilution factor=$5.0 \times 10^{-4}$
Rat No. 9, dilution factor=$1.0 \times 10^{-4}$
Rat No. 10 (Control Rat), sterile saline/no toxin After 14 days, the rats are sacrificed. The gastrocnemius muscle of each rat is removed, prepared and mounted on slides for analysis. The nuclei density (or nuclei area) of the Rat muscle is determined.

The nuclei density is plotted against the dose injected into the muscles of the rats. The $ED_{50}$ is determined from the plot. See FIG. 1.

EXAMPLE 2

Methods for Staining Muscle Cell Nucleus

Techniques of staining for the nuclei of muscles are well known. These include the Hematoxylin and Eosin (H&E), Propidium Iodine, DAPI, and Hoechst. See Manual of Histologic Staining Methods of the Armed Forces Institute of Pathology (Third Edition). American Registry of Pathology (Luna, Lee G., HT(ASCP) (editor)), McGraw Hill Publishers, New York 1960. Wang and Gerdes, J Mol Cell Cardiol 29, 1553-1565 (1997). Lim and Alvarez-Buylla, Proc. Natl. Acad. Sci. USA 96, 75267531, (1999).

Hematoxylin & Eosin

The staining procedure involves using deparaffinized sections, after which they are rehydrated. If the sections are Zenker-fixed, remove the mercuric chloride crystals with iodine and clear with sodium thiosulphate (hypo). Next, add Mayer's hematoxylin for 15 minutes. Wash in running tap water for 20 minutes.

Counterstain with eosin from 15 seconds to 2 minutes depending on the age of the eosin, and the depth of the counterstain desired. For even staining results, dip slides several times before allowing them to set in the eosin for the desired time. Then dehydrate in 95% and absolute alcohols, two changes of 2 minutes each or until excess eosin is removed. Check under a microscope. Clear in xylene, two changes of 2 minutes each, and mount in Permount or Histoclad.

The stains appear as follows: the nuclei appear blue, with some metachromasia Cytoplasm and various shades of pink identifying different tissue components The adhesives used to attach sections onto the slides (gelatin, egg albumen) sometimes stain, in areas around the section, with Mayor's hematoxylin. This gives the slides a slightly dark appearance but in no way affects the nuclear staining. To remedy this, use 10-12% glacial acetic acid in 95% alcohol, to "clean" the slides after Mayor's hematoxylin. Following with a few dips in saturated aqueous lithium carbonate, the nuclei become blue immediately. This is optional, for the 20-minute wash in running water is sufficient to blue the nuclei.

In one embodiment, the Sakura Finetek DRS-60 Stainer may be used in accordance with the present invention.

Staining Nucleus with Propidium Iodide (PI)

The muscle cells may be fixed with 4% PFA for 30 min at room temperature. Then the cells are to be washed 3 times, 5 min with PBS. Next, incubate cells for 5 min at room temperature in 1.25 ug/ml propidium idodide (Sigma Chemical Co., St. Louis, Mo.).

Staining Nucleus with DAPI

First, repeat the three steps from staining with Pi except the counterstain is done with DAPI. DAPI (4'-6-Diamidino-2-phenylindole2HCl') (Serva) Stock solution is prepared with 0.2 mg/ml of distilled water.

The staining solutions are prepared with 0.2-0.4 µg/ml of buffer PBS.

Flood with DAPI solution, cover with coverslip and incubate in the dark at room temp. for 5-15 mins. Then rinse briefly with PBS.

Staining Nucleus with Hoechst 33258

Fix the muscle cells with 4% PFA for 30 min at room temperature. Wash the cells 3 times for 5 min with PBS. Then incubate the cells for 5 min at room temperature in 0.5 µg/ml Hoechst 33258. Wash briefly with PBS.

EXAMPLE 3

Isolating the mRNAs of Electrically Coupled Factors

To determine the relative abundance of mRNAs specific for slow troponin I (sTNI), fast troponin I (fTnI), and each muscle regulatory factor (MRF), standard RNA isolation and Northern hybridization procedures are performed. Total RNA is isolated from frozen muscle samples by acid guanidinium isothiocyanate/phenol/chloroform extraction followed by isopropanol precipitation (Chomczynski and Sacchi, 1987). The RNA is obtained from mammals, for example rats or humans.

Analogous muscles of 4 to 6 different subjects is pooled. Total muscle RNA is isolated in a similar fashion and serves as a negative control. RNA samples (20 µg) are fractionated by electrophoresis through 1% agarose/formaldehyde gels (Lehrach et al., 1977), transferred to Nytran (Schleicher and Schuell, Keene, N.H.), and immobilized by UV crosslinking. Random primed cDNA probes (specific activity $\geq 1 \times 10^{*}8$ cpm/µg) then they are hybridized to the membranes at 65 C in 6×SSC (1×SSC consists of 0.15 M Tris-Cl, pH 7.5, 5×Denhardt's solution, 2 mM EDTA, pH 8.0, 0.5% SDS) and 100 µg/ml denatured salmon sperm DNA. The cDNA probes used in this study include rat MRF4 (Davis et al., 1987), rat myogenin (Wright, et al., 1989), human Myf-5 (Braun et al., 1989), and mouse fast and slow troponin I (Koppe et al., 1989). Following hybridization, all membranes are washed for 1 hr at 65 C. in 0.1×SSC, 0.2% SDS, except for those probed with Myf-5 and MyoD which are washed in 0.5×SSC, 0.2% SDS. In some instances, the hybridized probes are removed from the filters by washing the membranes in 5 mM Tris-Cl, pH 7.5, 0.2 mM EDTA, pH 8.0, 0.05% pyrophosphate, and 0.1×Denhardt's at 65 C for 1 to 2 hr. The filters are then rinsed briefly in 2×SSPE (1×SSPE consists of 0.15 M NaCl, 10 mM sodium phosphate, 1 mM EDTA, pH 7.4) after which additional hybridizations are performed. To quantitate autoradiograms obtained form Northern hybridization analyses, a densitometric evaluation is performed using an Ultrascan XL Laser Densitometer (Pharmacia LKB Biotechnology, Piscataway, N.J.). Multiple autoradiogram exposures are scanned to insure that band densities remained within the linear response range of the film.

Figure 2:
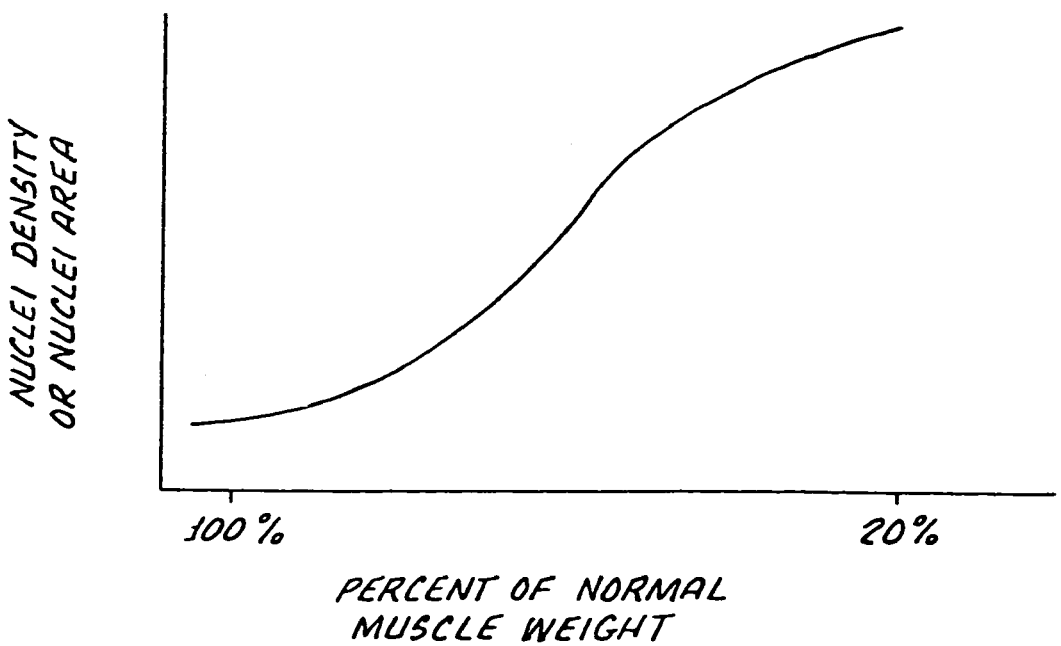
FIG. 2 shows that the nuclei area (within a discrete area) in a muscle is inversely proportional to the muscle mass.
Figure 3:
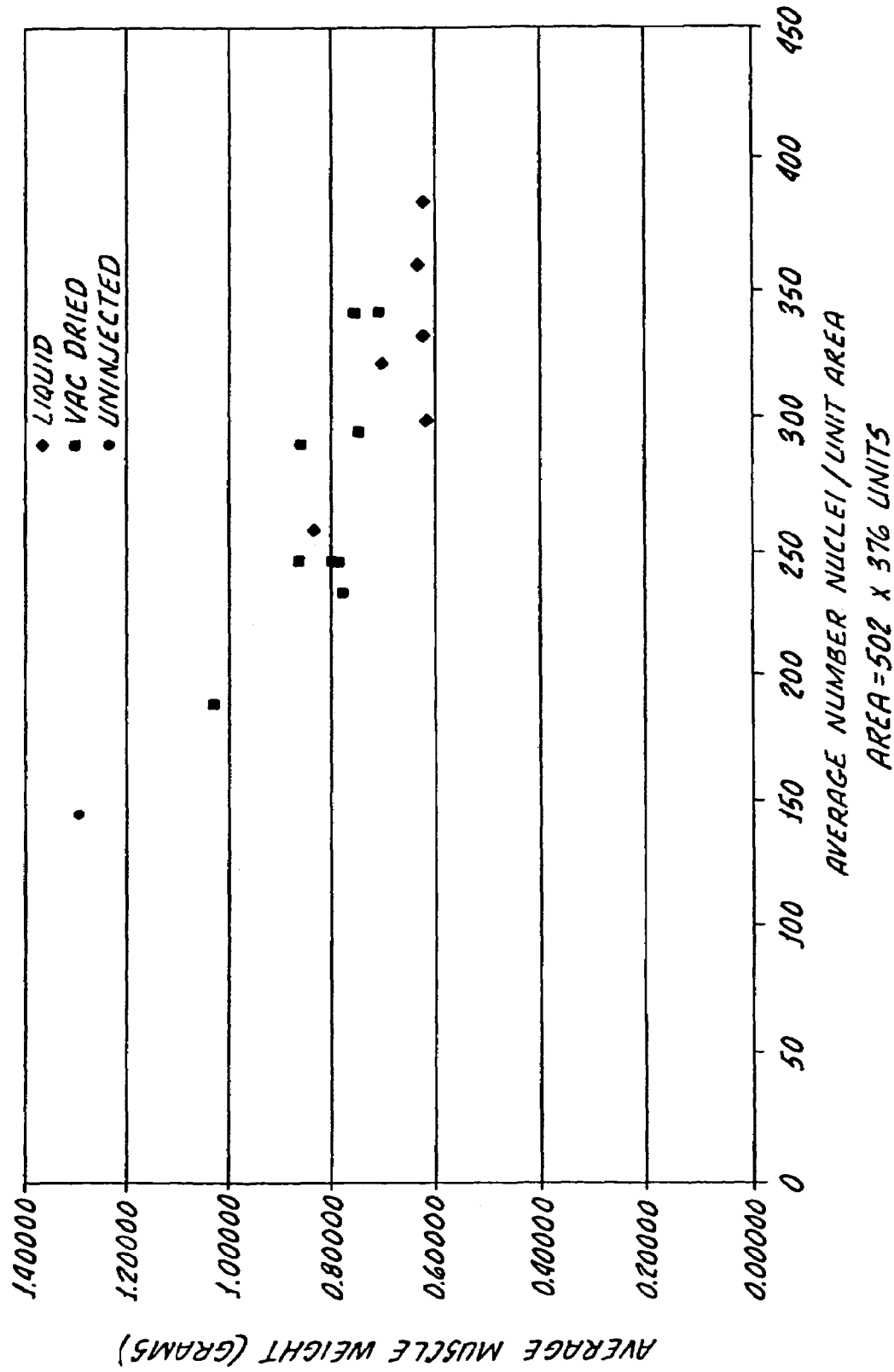
FIG. 3 shows that the nuclei number (within a discrete area) in a muscle is inversely proportional to the muscle mass.
Figure 4:
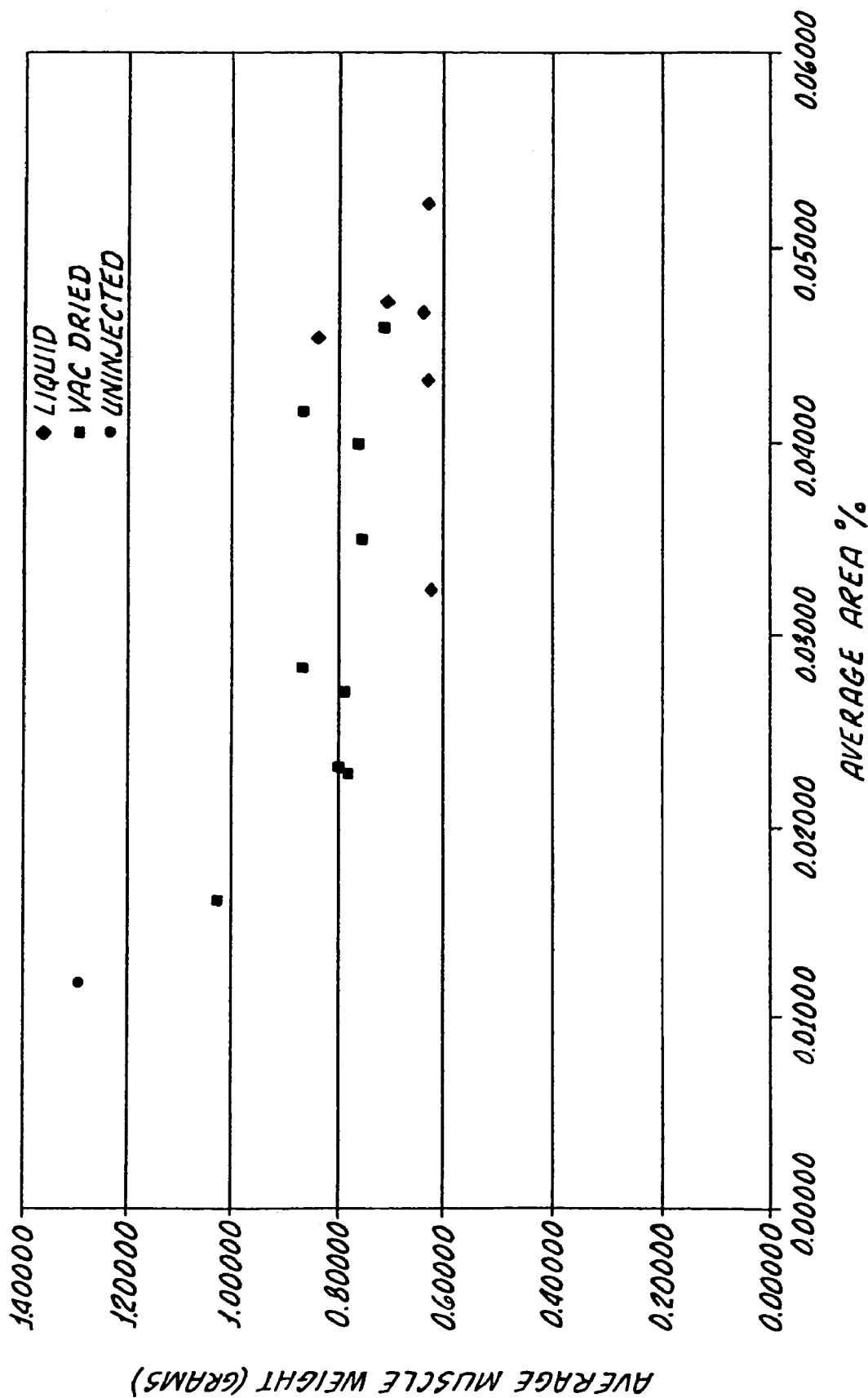
FIG. 4 shows that an increase in nuclei area corresponds to lower muscle mass.

II. Methods of Using Nuclear Index and/or Muscle Atrophy to Determine Toxin Potency and Diffusion The present invention provides for a faster, easier, more sensitive and more accurate method for assessing muscle atrophy as a parameter for determining toxin potency and/or diffusion. The method comprises the step of comparing a nuclear index of the muscle suspected of being atrophied to that of a muscle which is normal. Preferably, the present invention provides for a method of assessing muscle atrophy due to the effects of Clostridium toxin by comparing a nuclear index of the muscle injected with Clostridial toxin to that of an analogous muscle which is not injected with Clostridial toxin.

It is presently discovered that the nuclear index varies proportionately with the degree of muscle atrophy. For example, FIGS. 2 (and 3) shows that the nuclei (and nuclei number) in a muscle is inversely proportional to the muscle mass. FIG. 4 shows that an increase in nuclei area corresponds to lower muscle mass. Thus, the extent of changes in the nuclear index reveals the extent of muscle atrophy. For example, a small increase in nuclei density after an administration of botulinum toxin is indicative that the muscle has not atrophied much. Whereas, a large increase in nuclei is indicative that the muscle has significantly atrophied.

In one embodiment, the extent of changes in nuclear index, which is change in muscle weight and fiber diameter, of the various injected muscle will demonstrate the inherent activity of a toxin, for example botulinum toxin, at a therapeutically relevant site. In addition, the diffusion potential of the toxin protein in a given formulation may be quantitated within the same mammals by the extent of muscle atrophy of the muscles (of various fiber types) peripheral to the injection site.

EXAMPLE 4

Muscle Atrophy Assay

The extent of muscle atrophy in response to botulinum toxin treatment in terms of decreases in muscle weight and muscle fiber diameter can be determined using the methods of this invention.

Adult rats are injected intramuscularly with a single dose of botulinum toxin into the midbelly area (location of motor endplate) of each rat's left gastrocnemius muscle. Doses are at a low level of 0 to 2.5 U per rat (up to ~10 U/kg) to minimize systemic toxicity which can be a confounding factor for the evaluation of local pharmacologic effects. At a selected time point within two weeks of dosing, several muscles from the injected hind leg will be collected for gravimetric and histopathologic evaluations. Muscle collection includes muscles of different fiber types: the injected muscle (gastrocnemius), two muscles immediately adjacent to the injection site (biceps femoris and soleus), and two muscles further away from the injection site (peroneus and tibialis).

Muscle weight changes may be normalized against each rat's body weight. The extent of muscle weight decreases may be expressed by comparison with muscles from each rat's uninjected, contralateral leg or with placebo injected controls.

Histopathologic evaluation may involve qualitative assessment on a standard scale (grade 1 to 5, corresponding to minimal to maximal reduction in fiber diameter) or quantitative measurement with computer-assisted morphometric evaluation. See FIGS. 9 and 10.

EXAMPLE 5

Muscle Weight as a Measure of Botulinum Toxin Type A Potency and Diffusion

Female Sprague Dawley derived rats (young adult, about 250 grams in body weight) were injected with a single dose of a botulinum toxin type A complex (BOTOX®) into only the left gastrocnemius muscle. The individual doses injected into separate rat left gastrocnemius muscles were 0.04 unit, 0.07 unit, 0.12 unit, 0.21 unit, 0.37 unit, 0.65 unit and 1.1 units. Adjacent to the toxin injected left gastrocnemius muscle were the uninjected left biceps femoris and the uninjected left soleus muscles. The right gastrocnemius muscle, the right biceps femoris muscle and the right soleus muscle of each rat were not injected and were therefore retained as controls. Muscles from both (injected and uninjected) left and right hindlegs (gastrocnemius muscle), as well as the uninjected left and uninjected right biceps femoris and soleus muscles, were extracted at 14 days after dosing of the left gastrocnemius muscles and then weighed.

FIG. 11 shows the result of this experiment where the left gastrocnemius muscle of different rats was injected with varying amounts of a botulinum toxin type A. The y axis shows the ratio (as a percent) of the weight of the toxin injected left gastrocnemius muscle of the rat to the weight of the uninjected right gastrocnemius muscle of the same rat. The x axis shows the amount in units of the botulinum toxin type A that was injected into the left gastrocnemius muscle.

FIG. 12 shows the result of this experiment where the left gastrocnemius muscle of different rats was injected with varying amounts of a botulinum toxin type A. The y axis shows the ratio (as a percent) of the weight of the uninjected left biceps femoris muscle (which is adjacent to the toxin injected left gastrocnemius muscle of the rat) to the weight of the uninjected right biceps femoris muscle of the same rat. The x axis shows the amount in units of the botulinum toxin type A that was injected into the left gastrocnemius muscle.

FIG. 13 shows the result of this experiment where the left gastrocnemius muscle of different rats was injected with varying amounts of a botulinum toxin type A. The y axis shows the ratio (as a percent) of the weight of the uninjected left soleus muscle (which is adjacent to the toxin injected left gastrocnemius muscle of the rat) to the weight of the uninjected right soleus muscle of the same rat. The x axis shows the amount in units of the botulinum toxin type A that was injected into the left gastrocnemius muscle.

As shown by FIGS. 11-13 injection of BOTOX® caused muscle atrophy (and muscle weight decrease) at the injection muscle (left gastrocnemius) and adjacent (left bicep femoris and left soleus muscles) sites. The injected left gastrocnemius muscle showed an excellent dose-related decrease in muscle weight that was well modeled with a statistical function (4-parameter logistic regression). An ED50 (the dose required to reach 50% of the maximum possible level of response) for the muscle weight response was calculated (0.47 U/rat) and is associated with a very good confidence interval (standard error=0.03), showing therefore that this is a feasible and precise in vivo method for assessing pharmacologic potency of a botulinum toxin, such as BOTOX®. Muscle weight reduction is a more sensitive endpoint than lethality since the ED50 dose for rat muscle weight (0.47 U) is more than 2-fold lower than the mouse LD50 assay on a unit per animal basis. Muscles being injected showed a lower ED50 than the adjacent muscles (0.65 U for left biceps femoris and 1.16 U for left soleus) into which the toxin diffused from the injected gastrocnemius muscle. The ratio of ED50 of an adjacent muscle to the gastrocnemius can be used as a measure of the diffusion of BOTOX®. These data support the use of muscle weight to assess potency and diffusion in a single test system.

EXAMPLE 6

Quantification of Muscle Atrophy and Potency of One Type of Botulinum Toxin Obtained from Two Different Strains of *Clostridium* Bacterium Young female Sprague Dawley rats received injections of botulinum toxin type A. One group of rats (TX03006) received an intramuscular injection of BOTOX® in the left gastrocnemius, similar to that described in Example 5. A second group of rats (TX03007) received an intramuscular injection of DYSPORT® in the left gastrocnemius. The injection volume was 0.2 mL/kg. The injections were made in the lateral head and in the midbelly area of the left gastrocnemius.

Each group of rats (i.e., TX03006 and TX03007) included 5 rats per dosage of botulinum toxin. The dosages for BOTOX® were: 0.156, 0.313, 0.625, 1.25, 2.5, 5, 10, and 20 U/kg body weight. The dosages for DYSPORT® were: 0, 0.5, 1.0, 2.0, 4.0, 8.0, 16.0, 32.0, and 64.0 U/kg body weight.

Muscles from the injected leg and the control (i.e., contralateral) leg were dissected at 14 days after injection. Muscle weights were determined. The weight data was entered into computer software programs for statistical analysis and graphical presentation (SAS®, version 8.2; and SigmaPlot®, version 8).

The weight of the injected gastrocnemius was compared to the weight of the uninjected gastrocnemius for each animal (each animal served as its own control). Data were tightly distributed and were consistent with data from previous studies. The data for the BOTOX® group is illustrated in FIG. 14. The data for the DYSPORT® group is illustrated in FIG. 15. Using a 4-parameter logistic regression model, the muscle weight data were fitted for ED50 calculation. The ED50 is defined as the dose associated with a response half way between the maximum and minimum asymptotes for the gastrocnemius muscle.

An excellent curve fit was obtained with this model, and the correlation coefficient was nearly 1.0 for both groups of rats (0.94 for TX03006 and 0.96 for TX03007). The ED50 value for BOTOX® was 1.75±0.25 U/kg (mean±s.e.). The ED50 value for DYSPORT® was 7.97±1.54 U/kg (mean±s.e.).

Thus, DYSPORT® exhibited a potency value of 7.97 U/kg, and BOTOX® exhibited a potency value of 1.75 U/kg. These potency values correlate well with reported clinical potency differences of these two products. For example, BOTOX was shown to be nearly 5-fold more potent than DYSPORT®.

As discussed herein, it has been observed that when used clinically to treat various muscle disorders, BOTOX® and DYSPORT® have different potencies. For example, clinical work has demonstrated that BOTOX® has been reported to have a 2- to 10-fold greater potency than DYSPORT®. However, DYSPORT® and BOTOX® exhibit similar potencies when using the mouse IP LD50 assay (the lethality assay), described herein, which is the current product release assay for botulinum toxin products. In other words, the mouse IP LD50 potency data do not distinguish DYSPORT® and BOTOX®.

In comparison, using the muscle weight assay disclosed herein, the potency of BOTOX® was found to be 4.6-fold higher than DYSPORT®. This potency difference more closely reflects the potency difference observed between BOTOX® and DYSPORT® when used clinically.

EXAMPLE 7

Distinguishing Botulinum Toxin Type A From Botulinum Toxin Type B

The methods of Example 6 are repeated, except a composition containing botulinum toxin type B is injected instead of DYSPORT®. Botulinum toxin type B is injected at dosages of 0, 10, 100, 200, 500, 1000, 2000, 5000, and 10,000 U/kg. The ED50 of botulinum toxin type B is determined by analyzing the muscle weight data with statistical software. The ED50 of botulinum toxin type B is greater than the ED50 for BOTOX®.

EXAMPLE 8

Distinguishing Botulinum Toxin Type A From Botulinum Toxin Type E

The methods of Example 6 are repeated, except a composition containing botulinum toxin type E is injected instead of DYSPORT®. Botulinum toxin type E is injected at dosages of 0, 10, 20, 50, 100, 200, 500, and 1000 U/kg. The ED50 of botulinum toxin type E is determined by analyzing the muscle weight data with statistical software. The ED50 of botulinum toxin type B is greater than the ED50 for BOTOX®.

EXAMPLES 9-12

Distinguishing Botulinum Toxin Type A From Botulinum Toxin Types C, D, F, and G

The methods of Example 6 are repeated, except a composition containing either botulinum toxin type C, D, F, or G is injected instead of DYSPORT®. Botulinum toxin type C, D, F, or G is injected at dosages of 0, 10, 20, 50, 100, 200, 500, and 1000 U/kg. The ED50 of each of the botulinum toxin type C, D, F, and G is determined by analyzing the muscle weight data with statistical software. The ED50 for each of botulinum toxin type C, D, F, and G is greater than the ED50 for BOTOX®.

An assessment of potency of a botulinum toxin with the assays disclosed herein to measure muscle atrophy and muscle weight subsequent to an intramuscular (IM) injection of a botulinum toxin is more clinically relevant than the current standard. The current standard (mouse IP LD50 potency assay) involves an intraperitoneal (IP) injection followed by monitoring for mortality in the mouse. However, since botulinum toxin is typically used IM (never IP), intramuscular exposure is more clinically relevant. Furthermore, the IM approach allows calculation of an effective dose per unit of muscle mass (dose per gram of muscle), which can permit clinicians to determine how much of a botulinum toxin to inject into muscles of various sizes.

Additionally, the muscle weight and atrophy assay disclosed herein is a useful tool for assessing diffusion of a botulinum toxin, which is an important property to evaluate in new formulation development for botulinum toxins. A slight diffusion within the injected muscle is necessary to achieve a full therapeutic response while extensive diffusion to distal sites are always undesirable as this may result in serious adverse side effects. In optimizing a formulation, one has to understand the degree of desirable diffusion for treating a specific clinical condition. A determination of the weight and atrophy of muscles adjacent and distal to the injection site can provide critical information on whether a new formulation is potentially useful.

In addition or alternatively to the methods described above, the present methods may include one or more steps, such as (i) identifying a muscle suitable for intramuscular injection of a botulinum toxin, extraction, and weight determination; (ii) injecting into a targeted neuromuscular junction area (e.g., the lateral head or midbelly) of the gastrocnemius muscle to enhance or maximize the response to the botulinum toxin; (iii) collecting or extracting the injected muscle at a time effective in providing a stable response (such as about 14 days after injection; (iv) using the contralateral leg of the subject as a comparison or control to improve data quality and minimize the number of animals used to study potency differences; (v) using only animals of a single gender (such as female rats) to enhance consistency in muscle weight; and (vi) selecting an appropriate mathematical modeling technique to calculate the endpoint of interest, such as ED50.

The present methods provide an ability to distinguish potency differences between different botulinum toxin products that the lethality assay (mouse IP LD50 assay) cannot.

While this invention has been described with respect to various specific examples and embodiments, it is to be understood that the invention is not limited thereto and that it can be variously practiced with the scope of the following claims. All patents, applications, publications and references cited herein are incorporated by reference in their entireties.

What is claimed is:

1. A method for determining the potency of a Clostridial neurotoxin, comprising the steps of:
    administering different dosages of a Clostridial neurotoxin to a muscle of a plurality of animals to provide neurotoxic effect on the muscle;
    removing the muscle from the animals at a time when the neurotoxic effect has been achieved, wherein the muscle is removed about 2 weeks after administration of the Clostridial neurotoxin;
    constructing a dose response curve by correlating an amount of muscle atrophy of the muscle that was administered with a particular dose of the Clostridial neurotoxin, thereby determining the potency of the Clostridial neurotoxin.

2. The method of claim 1, wherein the atrophy is determined by weighing the muscle.

3. The method of claim 1, further comprising comparing the weight of the muscle to the weight of a control muscle.

4. The method of claim 1, wherein the muscle atrophy is determined by measuring muscle fiber diameter.

5. The method of claim 1, wherein the muscle atrophy is determined histopathologically.

6. The method of claim 1, further comprising repeating the steps in a plurality of animals.

7. The method of claim 6, further comprising calculating an ED50 from weight data obtained from the plurality of animals.

8. The method of claim 1, wherein the Clostridial neurotoxin is a botulinum toxin selected from the group consisting of botulinum toxin types A, B, C, D, E, F and G.

9. The method of claim 1, wherein the Clostridial neurotoxin is a botulinum toxin type A.

10. The method of claim 1, wherein the Clostridial neurotoxin is botulinum toxin type A and is administered at a dosage greater than 0 U/kg and less than about 10 U/kg.

11. The method of claim 1, wherein the muscle is a gastrocnemius muscle.

12. The method of claim 1, wherein the amount of muscle atrophy is determined by determining the nuclear index of the muscle.

* * * * *

UNITED STATES PATENT AND TRADEMARK OFFICE
CERTIFICATE OF CORRECTION

PATENT NO. : 7,229,605 B2  Page 1 of 3
APPLICATION NO. : 10/918845
DATED : June 12, 2007
INVENTOR(S) : James M. Holland et al.

It is certified that error appears in the above-identified patent and that said Letters Patent is hereby corrected as shown below:

On the Title Page, Item -56- on page 2, under "Other Publications", line 22, delete "court" and insert -- cord --, therefor.

On the Title Page, Item -56- on page 2, under "Other Publications", line 25, delete "carious" and insert -- various --, therefor.

On the Title Page, Item -56- on page 2, under "Other Publications", line 27, delete "pharmocol," and insert -- pharmacol, --, therefor.

On the Title Page, Item -56- on page 2, under "Other Publications", line 37, delete "anc" and insert -- and --, therefor.

On the Title Page, Item -56- on page 2, under "Other Publications", line 40, delete "byb" and insert -- by --, therefor.

On the Title Page, Item -56- on page 2, under "Other Publications", line 42, delete "Mar" and insert -- Mar. --, therefor.

On the Title Page, Item -56- on page 2, under "Other Publications", line 50, delete "7256-7531," and insert -- 7526-7531, --, therefor.

On the Title Page, Item -56- on page 2, under "Other Publications", line 52, delete "$3_{rd}$" and insert -- $3^{rd}$ --, therefor.

On the Title Page, Item -56- on page 2, under "Other Publications", line 60, delete "Marjarma" and insert -- Marjama --, therefor.

On the Title Page, Item -56- on page 2, under "Other Publications", line 61, after "2000" insert -- ; --.

On the Title Page, Item -56- on page 2, under "Other Publications", line 2, delete "botulimun" and insert -- botulinum --, therefor.

On the Title Page, Item -56- on page 2, under "Other Publications", line 4, after "A blocks" delete "A blocks".

On the Title Page, Item -56- on page 2, under "Other Publications", line 6, after "1987" insert -- ; --.

UNITED STATES PATENT AND TRADEMARK OFFICE
CERTIFICATE OF CORRECTION

PATENT NO. : 7,229,605 B2
APPLICATION NO. : 10/918845
DATED : June 12, 2007
INVENTOR(S) : James M. Holland et al.

It is certified that error appears in the above-identified patent and that said Letters Patent is hereby corrected as shown below:

On the Title Page, Item -56- on page 2, under "Other Publications", line 7, delete "chlostridium" and insert -- clostridium --, therefor.

On the Title Page, Item -56- on page 2, under "Other Publications", line 24, delete "botilinum" and insert -- botulinum --, therefor.

On the Title Page, Item -56- on page 2, under "Other Publications", line 37, delete "thioyanate" and insert -- thiocyanate --, therefor.

On the Title Page, Item -56- on page 2, under "Other Publications", line 40, delete "978-1000," and insert -- 987-1000, --, therefor.

On the Title Page, Item -56- on page 2, under "Other Publications", line 52, delete "atropy" and insert -- atrophy --, therefor.

On the Title Page, Item -56- on page 2, under "Other Publications", line 62, delete "Postate," and insert -- Prostate, --, therefor.

On the Title Page, Item -56- on page 2, under "Other Publications", line 71, delete "Hott,." and insert -- Hott, --, therefor.

On the Title Page, Item -56- on page 3, under "Other Publications", line 3, delete "Neromuscular" and insert -- Neuromuscular --, therefor.

On the Title Page, Item -56- on page 3, under "Other Publications", line 5, delete "neurogulin." and insert -- neuregulin. --, therefor.

On the Title Page, Item -56- on page 3, under "Other Publications", line 6, delete "Reseach," and insert -- Research, --, therefor.

On Sheet 13 of 17, Fig. 11, (Above X-axis), line 1, delete "GASTRONEMIUS" and insert -- GASTROCNEMIUS --, therefor.

In column 7, line 8, delete "norepinephine." and insert -- norepinephrine. --, therefor.

In column 8, line 2, delete "Pharacol" and insert -- Pharmacol --, therefor.

UNITED STATES PATENT AND TRADEMARK OFFICE
CERTIFICATE OF CORRECTION

PATENT NO. : 7,229,605 B2
APPLICATION NO. : 10/918845
DATED : June 12, 2007
INVENTOR(S) : James M. Holland et al.

It is certified that error appears in the above-identified patent and that said Letters Patent is hereby corrected as shown below:

In column 8, line 10, delete "5,183,462,)." and insert -- 5,183,462). --, therefor.

In column 14, line 42, delete "staining," and insert -- staining. --, therefor.

In column 17, line 41, after "components" insert -- . --.

In column 17, line 58, delete "idodide" and insert -- iodide --, therefor.

In column 18, lines 32, 39 and 44, delete "65C" and insert -- 65 °C --, therefor.

Signed and Sealed this

Twenty-second Day of July, 2008

JON W. DUDAS
*Director of the United States Patent and Trademark Office*